(12) United States Patent
Li et al.

(10) Patent No.: US 11,708,368 B2
(45) Date of Patent: Jul. 25, 2023

(54) CRYSTAL FORM OF ETHYL (S)-3-(8-BROMO-1-METHYL-6-(PYRIDIN-2-YL)-4H-BENZO[F]IMIDAZO[1,2-A][1,4] DIAZEPIN-4-YL)PROPANOATE HYDROCHLORIDE

(71) Applicant: JIANGSU NHWALUOKANG PHARMACEUTICAL RESEARCH AND DEVELOPMENT CO., LTD., Jiangsu (CN)

(72) Inventors: Qingeng Li, Chongqing (CN); Chen Duan, Chongqing (CN); Tao Wang, Chongqing (CN); Jian Liao, Chongqing (CN); Changwen Li, Chongqing (CN); Chao Hao, Chongqing (CN)

(73) Assignee: JIANGSU NHWALUOKANG PHARMACEUTICAL RESEARCH AND DEVELOPMENT CO., LTD., Xuzhou (CN)

( * ) Notice: Subject to any disclaimer, the term of this patent is extended or adjusted under 35 U.S.C. 154(b) by 212 days.

(21) Appl. No.: 16/969,224

(22) PCT Filed: Feb. 13, 2019

(86) PCT No.: PCT/CN2019/074935
§ 371 (c)(1),
(2) Date: Aug. 12, 2020

(87) PCT Pub. No.: WO2019/158075
PCT Pub. Date: Aug. 22, 2019

(65) Prior Publication Data
US 2021/0002283 A1    Jan. 7, 2021

(30) Foreign Application Priority Data

Feb. 13, 2018  (CN) .......................... 201810151979.0

(51) Int. Cl.
*A61K 31/519* (2006.01)
*C07D 487/04* (2006.01)
*A61K 9/00* (2006.01)

(52) U.S. Cl.
CPC .......... *C07D 487/04* (2013.01); *A61K 9/0019* (2013.01); *C07B 2200/13* (2013.01)

(58) Field of Classification Search
CPC ........................... A61K 31/519; C07D 487/04
USPC ........................................... 514/220; 540/562
See application file for complete search history.

(56) References Cited

FOREIGN PATENT DOCUMENTS

| CN | 103347519 A | 10/2013 |
|---|---|---|
| CN | 107266452 A | 10/2017 |
| WO | 2016011943 A1 | 1/2016 |

*Primary Examiner* — Douglas M Willis
(74) *Attorney, Agent, or Firm* — Dentons Davis Brown; Matthew Coryell

(57) ABSTRACT

The present invention provides a crystalline form of a benzodiazepine derivative hydrochloride of Formula I or its ethanolate, wherein R is methyl or ethyl. The present invention also provides a method of preparing the crystal form of the compound of Formula I and a pharmaceutical composition comprising the crystal form.

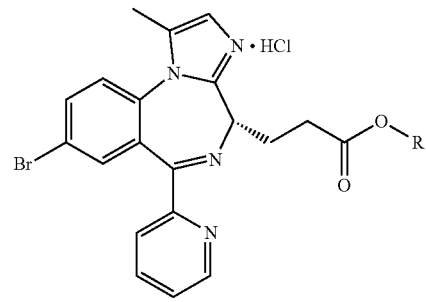

Formula I

22 Claims, 24 Drawing Sheets

Fig. 3: An X-ray powder diffraction pattern of the crystal of a compound of Formula I wherein R=CH3 (CNS-7056A2017120401)

CNS-7056A2017120401 batch.raw

| Angle | d value | Intensity | Intensity | Angle | d value | Intensity | Intensity |
|---|---|---|---|---|---|---|---|
| 6.805 | 12.97919 | 1271 | 57.5 | | | | |
| 8.114 | 10.88803 | 739 | 33.4 | | | | |
| 8.934 | 9.88987 | 2211 | 100.0 | | | | |
| 9.858 | 8.96523 | 855 | 38.7 | | | | |
| 13.393 | 6.60553 | 1430 | 64.7 | | | | |
| 14.725 | 6.01115 | 885 | 40.0 | | | | |
| 17.470 | 5.07225 | 1003 | 45.4 | | | | |
| 19.383 | 4.57577 | 1023 | 46.3 | | | | |
| 20.767 | 4.27392 | 1888 | 85.4 | | | | |
| 21.225 | 4.18258 | 1856 | 83.9 | | | | |
| 22.424 | 3.96163 | 1651 | 74.7 | | | | |
| 23.034 | 3.85809 | 1467 | 66.4 | | | | |
| 24.203 | 3.67431 | 1391 | 62.9 | | | | |
| 25.937 | 3.43242 | 1062 | 48.0 | | | | |
| 26.384 | 3.37533 | 1004 | 45.4 | | | | |
| 27.731 | 3.2144 | 1506 | 68.1 | | | | |
| 28.305 | 3.15041 | 1247 | 56.4 | | | | |

FIG. 3

Fig. 4: An X-ray powder diffraction pattern of the crystal of a compound of Formula I wherein R=CH₃ (CNS-7056AG20171225)

CNS-7056AG20171225 batch.raw

| Angle | d value | Intensity | Intensity | Angle | d value | Intensity | Intensity |
|---|---|---|---|---|---|---|---|
| 6.801 | 12.98626 | 1150 | 49.7 | | | | |
| 8.932 | 9.89249 | 1701 | 73.5 | | | | |
| 9.870 | 8.95458 | 2021 | 57.4 | | | | |
| 13.372 | 6.61614 | 1306 | 56.5 | | | | |
| 14.688 | 6.02614 | 1339 | 57.9 | | | | |
| 15.178 | 5.83255 | 846 | 36.6 | | | | |
| 16.144 | 5.48593 | 1077 | 46.6 | | | | |
| 17.476 | 5.07057 | 834 | 36.1 | | | | |
| 18.034 | 4.9148 | 790 | 34.2 | | | | |
| 19.359 | 4.58133 | 1228 | 53.1 | | | | |
| 20.019 | 4.43192 | 768 | 33.2 | | | | |
| 20.762 | 4.27478 | 1645 | 71.1 | | | | |
| 21.249 | 4.17803 | 1550 | 67.0 | | | | |
| 22.188 | 4.00329 | 1572 | 68.0 | | | | |
| 22.384 | 3.96856 | 1435 | 62.0 | | | | |
| 23.062 | 3.85339 | 2313 | 100.0 | | | | |
| 24.205 | 3.67402 | 1226 | 53.0 | | | | |
| 25.165 | 3.536 | 1067 | 46.1 | | | | |
| 25.932 | 3.43309 | 1383 | 59.8 | | | | |
| 26.358 | 3.37859 | 1122 | 48.5 | | | | |
| 27.734 | 3.214 | 1495 | 64.6 | | | | |
| 28.302 | 3.15084 | 1124 | 48.6 | | | | |
| 34.130 | 2.62494 | 738 | 31.9 | | | | |

FIG. 4

Fig. 5: An X-ray powder diffraction pattern of the crystal of a compound of Formula I wherein R=CH$_2$CH$_3$ (EL-001A2017120401)

EL-001A2017120401 batch.raw

| Angle | d value | Intensity | Intensity | Angle | d value | Intensity | Intensity |
|---|---|---|---|---|---|---|---|
| 6.827 | 12.93666 | 3943 | 58.9 | 29.345 | 3.0411 | 1178 | 17.6 |
| 7.394 | 11.94606 | 6398 | 95.5 | 30.301 | 2.94732 | 633 | 9.5 |
| 9.522 | 9.2809 | 1805 | 27.0 | 30.602 | 2.91901 | 703 | 10.5 |
| 11.671 | 7.576 | 598 | 8.9 | 31.317 | 2.85394 | 1076 | 16.1 |
| 12.195 | 7.25217 | 536 | 8.0 | 32.633 | 2.7418 | 596 | 8.9 |
| 13.701 | 6.45774 | 6696 | 100.0 | 34.434 | 2.60242 | 605 | 9.0 |
| 15.086 | 5.86803 | 1031 | 15.4 | 35.461 | 2.52938 | 487 | 7.3 |
| 15.403 | 5.74786 | 1514 | 22.6 | 36.084 | 2.48713 | 530 | 7.9 |
| 17.745 | 4.9944 | 517 | 7.7 | 38.018 | 2.36497 | 529 | 7.9 |
| 18.086 | 4.9009 | 742 | 11.1 | 38.712 | 2.32411 | 484 | 7.2 |
| 18.679 | 4.74671 | 1421 | 21.2 | 39.956 | 2.25457 | 558 | 8.3 |
| 19.089 | 4.64555 | 1006 | 15.0 | 41.294 | 2.181455 | 541 | 8.1 |
| 20.292 | 4.37287 | 771 | 11.5 | 43.327 | 2.08666 | 628 | 9.4 |
| 20.656 | 4.29666 | 1516 | 22.6 | 44.053 | 2.05392 | 502 | 7.5 |
| 21.169 | 4.19365 | 1517 | 22.7 | 45.229 | 2.00323 | 422 | 6.3 |
| 22.101 | 4.01881 | 2392 | 35.7 | | | | |
| 22.660 | 3.92092 | 3074 | 45.9 | | | | |
| 23.245 | 3.82357 | 835 | 12.5 | | | | |
| 23.588 | 3.76876 | 1701 | 25.4 | | | | |
| 25.088 | 3.54673 | 2283 | 34.1 | | | | |
| 25.552 | 3.48331 | 1653 | 24.7 | | | | |
| 25.837 | 3.44553 | 1013 | 15.1 | | | | |
| 27.264 | 3.26834 | 1709 | 25.5 | | | | |
| 27.695 | 3.21842 | 1054 | 15.7 | | | | |
| 28.169 | 3.16533 | 1649 | 24.6 | | | | |

FIG. 5

Fig. 6: An X-ray powder diffraction pattern of the crystal of a compound of Formula I wherein R=CH2CH3 (EL-001A2017120801)

EL-001A2017120801 batch.raw

| Angle | d value | Intensity | Angle | d value | Intensity | Intensity |
|---|---|---|---|---|---|---|
| 6.957 | 12.69556 | 3425 | 41.3 | 31.364 | 2.84979 | 1019 | 12.3 |
| 7.446 | 11.8624 | 5298 | 63.8 | 32.707 | 2.73579 | 648 | 7.8 |
| 9.606 | 9.19977 | 2020 | 24.3 | 34.363 | 2.60764 | 752 | 9.1 |
| 13.709 | 6.4542 | 8299 | 100.0 | 36.983 | 2.42872 | 763 | 9.2 |
| 14.017 | 6.31288 | 1963 | 23.7 | 41.277 | 2.18543 | 634 | 7.6 |
| 15.007 | 5.89883 | 863 | 10.4 | | | | |
| 15.502 | 5.71166 | 1597 | 19.2 | | | | |
| 18.155 | 4.88238 | 1028 | 12.4 | | | | |
| 18.796 | 4.71745 | 1638 | 19.7 | | | | |
| 19.170 | 4.62617 | 1193 | 14.4 | | | | |
| 20.282 | 4.37485 | 902 | 10.9 | | | | |
| 20.740 | 4.27932 | 1424 | 17.2 | | | | |
| 21.210 | 4.18552 | 1946 | 23.4 | | | | |
| 22.213 | 3.9988 | 2967 | 35.8 | | | | |
| 22.746 | 3.9062 | 2823 | 34.0 | | | | |
| 23.558 | 3.77349 | 1183 | 14.3 | | | | |
| 25.177 | 3.5343 | 2653 | 32.0 | | | | |
| 25.668 | 3.46783 | 1496 | 18.0 | | | | |
| 26.987 | 3.30123 | 1225 | 14.8 | | | | |
| 27.314 | 3.26244 | 1653 | 19.9 | | | | |
| 27.755 | 3.21161 | 1123 | 13.5 | | | | |
| 28.305 | 3.15042 | 1498 | 18.1 | | | | |
| 29.349 | 3.04075 | 1420 | 17.1 | | | | |
| 29.782 | 2.99754 | 706 | 8.5 | | | | |
| 30.737 | 2.90652 | 612 | 7.4 | | | | |

FIG. 6

Fig. 7: An X-ray powder diffraction pattern of the crystal of a compound of Formula I wherein R=CH₂CH₃ (EL-001A20180105)

EL-001A20180105 batch.raw

| Angle | d value | Intensity | Intensity | Angle | d value | Intensity | Intensity |
|---|---|---|---|---|---|---|---|
| 6.874 | 12.84864 | 2319 | 14.2 | 34.305 | 2.61195 | 898 | 5.5 |
| 7.369 | 11.9872 | 7215 | 44.3 | 41.195 | 2.18957 | 730 | 4.5 |
| 9.523 | 9.27953 | 2253 | 13.8 | 43.034 | 2.10018 | 903 | 5.5 |
| 13.626 | 6.49317 | 16300 | 100.0 | 52.785 | 1.73288 | 468 | 2.9 |
| 14.907 | 5.93806 | 1284 | 7.9 | | | | |
| 15.439 | 5.73474 | 1213 | 7.4 | | | | |
| 18.082 | 4.90188 | 824 | 5.1 | | | | |
| 18.712 | 4.73821 | 1201 | 7.4 | | | | |
| 19.089 | 4.6456 | 960 | 5.9 | | | | |
| 20.213 | 4.38971 | 1594 | 9.8 | | | | |
| 20.664 | 4.29497 | 1187 | 7.3 | | | | |
| 21.107 | 4.20578 | 2537 | 15.6 | | | | |
| 22.102 | 4.01858 | 1823 | 11.2 | | | | |
| 22.642 | 3.92401 | 1945 | 11.9 | | | | |
| 23.494 | 3.78352 | 1267 | 7.8 | | | | |
| 24.289 | 3.66145 | 691 | 4.2 | | | | |
| 25.090 | 3.54633 | 1498 | 9.2 | | | | |
| 25.540 | 3.48498 | 947 | 5.8 | | | | |
| 26.918 | 3.30955 | 1541 | 9.5 | | | | |
| 27.219 | 3.27364 | 1594 | 9.8 | | | | |
| 27.625 | 3.22644 | 1135 | 7.0 | | | | |
| 28.220 | 3.15981 | 806 | 4.9 | | | | |
| 29.276 | 3.04813 | 1529 | 9.4 | | | | |
| 31.202 | 2.86429 | 1161 | 7.1 | | | | |
| 32.624 | 2.74253 | 587 | 3.6 | | | | |

FIG. 7

Fig. 8: An X-ray powder diffraction pattern of the crystal of a compound of Formula I wherein R=CH2CH3 (EL-001A20180101801)

EL-001A2018010801 batch.raw

| Angle | d value | Intensity | Intensity | Angle | d value | Intensity | Intensity |
|---|---|---|---|---|---|---|---|
| 6.827 | 12.9378 | 2063 | 19.8 | 34.256 | 2.61554 | 747 | 7.2 |
| 7.314 | 12.07635 | 4350 | 41.8 | 41.165 | 2.19113 | 608 | 5.8 |
| 9.460 | 9.34114 | 2064 | 19.8 | | | | |
| 13.559 | 6.52507 | 10398 | 100.0 | | | | |
| 13.879 | 6.37572 | 1649 | 15.9 | | | | |
| 14.844 | 5.96308 | 1004 | 9.7 | | | | |
| 15.373 | 5.75899 | 1271 | 12.2 | | | | |
| 18.049 | 4.91095 | 899 | 8.6 | | | | |
| 18.654 | 4.75298 | 1228 | 11.8 | | | | |
| 19.046 | 4.65601 | 1035 | 10.0 | | | | |
| 20.151 | 4.40315 | 1188 | 11.4 | | | | |
| 20.608 | 4.30636 | 1201 | 11.6 | | | | |
| 21.047 | 4.21763 | 1834 | 17.6 | | | | |
| 22.086 | 4.02154 | 1995 | 19.2 | | | | |
| 22.630 | 3.92612 | 2173 | 20.9 | | | | |
| 23.420 | 3.79534 | 1155 | 11.1 | | | | |
| 25.056 | 3.55109 | 1823 | 17.5 | | | | |
| 25.515 | 3.48824 | 1065 | 10.2 | | | | |
| 26.866 | 3.31583 | 1168 | 11.2 | | | | |
| 27.183 | 3.27779 | 1446 | 13.9 | | | | |
| 27.591 | 3.23031 | 1011 | 9.7 | | | | |
| 28.191 | 3.16295 | 984 | 9.5 | | | | |
| 29.223 | 3.05356 | 1404 | 13.5 | | | | |
| 31.151 | 2.86883 | 1035 | 10.0 | | | | |
| 32.567 | 2.74722 | 568 | 5.5 | | | | |

FIG. 8

Fig. 9: An X-ray powder diffraction pattern of the crystal of a compound of Formula I wherein R=CH$_2$CH$_3$ (EL-001A20180130)

EL-001A20180130 batch.raw

| Angle | d value | Intensity | Intensity | Angle | d value | Intensity | Intensity |
|---|---|---|---|---|---|---|---|
| 7.409 | 11.922 | 11726 | 52.0 | 30.323 | 2.94524 | 2095 | 9.3 |
| 9.241 | 9.56258 | 22563 | 100.0 | 30.818 | 2.89904 | 1498 | 6.6 |
| 9.518 | 9.28439 | 3802 | 16.9 | 34.975 | 2.5634 | 1438 | 6.4 |
| 11.691 | 7.56367 | 2674 | 11.9 | 36.049 | 2.48944 | 1464 | 6.5 |
| 12.712 | 6.95804 | 4829 | 21.4 | 39.210 | 2.29575 | 1306 | 5.8 |
| 13.636 | 6.48856 | 12388 | 54.9 | | | | |
| 14.459 | 6.12121 | 1389 | 6.2 | | | | |
| 15.061 | 5.8779 | 5138 | 22.8 | | | | |
| 16.698 | 5.30506 | 1199 | 5.3 | | | | |
| 17.396 | 5.09371 | 2222 | 9.8 | | | | |
| 18.298 | 4.84452 | 7795 | 34.5 | | | | |
| 18.722 | 4.73582 | 6020 | 26.7 | | | | |
| 19.156 | 4.62951 | 2108 | 9.3 | | | | |
| 20.444 | 4.34057 | 2063 | 9.1 | | | | |
| 20.900 | 4.247 | 3115 | 13.8 | | | | |
| 21.588 | 4.11314 | 7613 | 33.7 | | | | |
| 22.180 | 4.0047 | 4826 | 21.4 | | | | |
| 22.602 | 3.93083 | 2755 | 12.2 | | | | |
| 23.650 | 3.75897 | 3835 | 17.0 | | | | |
| 24.261 | 3.66565 | 2327 | 10.3 | | | | |
| 25.735 | 3.45898 | 4878 | 21.6 | | | | |
| 26.404 | 3.37276 | 3590 | 15.9 | | | | |
| 27.133 | 3.28385 | 2120 | 9.4 | | | | |
| 28.430 | 3.13369 | 2283 | 10.1 | | | | |
| 29.348 | 3.04084 | 2391 | 10.6 | | | | |

FIG. 9

Fig. 10: An X-ray powder diffraction pattern of the crystal of a compound of Formula I wherein R=CH2CH3 (EL-001AG2017121801)

EL-001AG2017121801 batch.raw

| Angle | d value | Intensity | Intensity | Angle | d value | Intensity | Intensity |
|---|---|---|---|---|---|---|---|
| 6.933 | 12.73974 | 1748 | 24.0 | 29.372 | 3.03845 | 1003 | 13.8 |
| 7.453 | 11.85259 | 3574 | 49.0 | 29.713 | 3.00435 | 810 | 11.1 |
| 9.379 | 9.42178 | 1247 | 17.1 | 31.298 | 2.85564 | 838 | 11.5 |
| 9.644 | 9.16396 | 1976 | 27.1 | 34.384 | 2.60611 | 616 | 8.4 |
| 12.366 | 7.15192 | 623 | 8.5 | 41.307 | 2.18389 | 491 | 6.7 |
| 12.789 | 6.91619 | 448 | 6.1 | | | | |
| 13.727 | 6.44587 | 7292 | 100.0 | | | | |
| 15.478 | 5.72031 | 867 | 11.9 | | | | |
| 18.197 | 4.87129 | 1028 | 14.1 | | | | |
| 18.535 | 4.78307 | 1119 | 15.3 | | | | |
| 18.785 | 4.72012 | 1018 | 14.0 | | | | |
| 19.167 | 4.62683 | 770 | 10.6 | | | | |
| 20.282 | 4.37493 | 857 | 11.8 | | | | |
| 20.717 | 4.28407 | 1034 | 14.2 | | | | |
| 21.170 | 4.19337 | 1427 | 19.6 | | | | |
| 22.217 | 3.99801 | 1903 | 26.1 | | | | |
| 22.747 | 3.90612 | 1557 | 21.4 | | | | |
| 23.561 | 3.77729 | 938 | 12.9 | | | | |
| 24.327 | 3.65581 | 817 | 11.2 | | | | |
| 25.173 | 3.53490 | 1573 | 21.6 | | | | |
| 25.698 | 3.46388 | 1020 | 14.0 | | | | |
| 26.999 | 3.29982 | 896 | 12.3 | | | | |
| 27.305 | 3.26353 | 1075 | 14.7 | | | | |
| 27.764 | 3.21065 | 894 | 12.3 | | | | |
| 28.299 | 3.15117 | 808 | 11.1 | | | | |

FIG. 10

Fig. 11: An X-ray powder diffraction pattern of the crystal of a compound of Formula I wherein R=CH$_2$CH$_3$ (EL-001AG2017122101)

EL-001AG2017122101 batch.raw

| Angle | d value | Intensity | Intensity | Angle | d value | Intensity | Intensity |
|---|---|---|---|---|---|---|---|
| 6.913 | 12.77694 | 1609 | 31.1 | | | | |
| 7.9383 | 11.96441 | 3092 | 59.8 | | | | |
| 9.565 | 9.23925 | 1631 | 31.5 | | | | |
| 10.514 | 8.40753 | 578 | 11.2 | | | | |
| 12.146 | 7.28114 | 511 | 9.9 | | | | |
| 13.363 | 6.62045 | 3120 | 60.3 | | | | |
| 13.655 | 6.47982 | 5174 | 100.0 | | | | |
| 14.803 | 5.97974 | 825 | 15.9 | | | | |
| 17.167 | 5.16102 | 506 | 9.8 | | | | |
| 18.113 | 4.89368 | 812 | 15.7 | | | | |
| 18.725 | 4.735 | 745 | 14.4 | | | | |
| 19.085 | 4.64661 | 753 | 14.6 | | | | |
| 20.242 | 4.38346 | 804 | 15.5 | | | | |
| 20.674 | 4.29281 | 968 | 18.7 | | | | |
| 21.156 | 4.19622 | 1200 | 23.2 | | | | |
| 22.168 | 4.00688 | 1807 | 34.9 | | | | |
| 22.688 | 3.91619 | 1601 | 30.9 | | | | |
| 23.502 | 3.78231 | 1045 | 20.2 | | | | |
| 25.140 | 3.5395 | 1463 | 28.3 | | | | |
| 25.597 | 3.47727 | 1006 | 19.4 | | | | |
| 26.987 | 3.30124 | 892 | 17.2 | | | | |
| 27.251 | 3.26988 | 1165 | 22.5 | | | | |
| 29.308 | 3.04487 | 1028 | 19.9 | | | | |
| 30.546 | 2.92422 | 693 | 13.4 | | | | |
| 31.293 | 2.85609 | 764 | 14.8 | | | | |

FIG. 11

Fig. 12: An X-ray powder diffraction pattern of the crystal of a compound of Formula I wherein R=CH$_2$CH$_3$ (EL-001AG20171227O2LJ)

EL-001AG20171227O2LJ batch.raw

| Angle | d value | Intensity | Intensity | Angle | d value | Intensity | Intensity |
|---|---|---|---|---|---|---|---|
| 6.843 | 12.90674 | 2176 | 17.5 | 41.205 | 2.1891 | 607 | 4.9 |
| 7.344 | 12.02713 | 5269 | 42.3 | 43.050 | 2.09946 | 775 | 6.2 |
| 9.491 | 9.31071 | 1834 | 14.7 | | | | |
| 13.616 | 6.49803 | 12467 | 100.0 | | | | |
| 14.907 | 5.93813 | 970 | 7.8 | | | | |
| 15.411 | 5.74485 | 1218 | 9.8 | | | | |
| 18.043 | 4.91236 | 979 | 7.9 | | | | |
| 18.673 | 4.74807 | 1038 | 8.3 | | | | |
| 19.045 | 4.66561 | 992 | 8.0 | | | | |
| 20.195 | 4.39357 | 1273 | 10.2 | | | | |
| 20.625 | 4.30295 | 1100 | 8.8 | | | | |
| 21.087 | 4.2097 | 1871 | 15.0 | | | | |
| 22.088 | 4.02122 | 2006 | 16.1 | | | | |
| 22.614 | 3.92884 | 2204 | 17.7 | | | | |
| 23.460 | 3.78899 | 1192 | 9.6 | | | | |
| 25.058 | 3.55087 | 1700 | 13.6 | | | | |
| 25.542 | 3.48465 | 1231 | 9.9 | | | | |
| 26.918 | 3.30956 | 1419 | 11.4 | | | | |
| 27.206 | 3.27514 | 1570 | 12.6 | | | | |
| 27.628 | 3.22608 | 1109 | 8.9 | | | | |
| 28.193 | 3.16269 | 929 | 7.5 | | | | |
| 29.246 | 3.05118 | 1442 | 11.6 | | | | |
| 31.204 | 2.86411 | 1102 | 8.8 | | | | |
| 32.608 | 2.7439 | 603 | 4.8 | | | | |
| 34.305 | 2.61191 | 825 | 6.6 | | | | |

FIG. 12

Fig. 13: An X-ray powder diffraction pattern of the crystal of a compound of Formula I wherein R=CH$_2$CH$_3$ (EL-001AG2018010201)

EL-001AG2018010201 batch.raw

| Angle | d value | Intensity | Intensity | Angle | d value | Intensity | Intensity |
|---|---|---|---|---|---|---|---|
| 6.664 | 13.25309 | 1823 | 36.0 | | | | |
| 7.309 | 12.08461 | 3282 | 64.8 | | | | |
| 9.400 | 9.40061 | 1187 | 23.4 | | | | |
| 11.593 | 7.62709 | 594 | 11.7 | | | | |
| 12.097 | 7.31054 | 560 | 11.1 | | | | |
| 13.640 | 6.48685 | 5062 | 100.0 | | | | |
| 15.061 | 5.87784 | 1197 | 23.6 | | | | |
| 15.398 | 5.7497 | 690 | 13.6 | | | | |
| 18.022 | 4.91819 | 937 | 18.5 | | | | |
| 18.996 | 4.66818 | 1240 | 24.5 | | | | |
| 20.515 | 4.32579 | 1693 | 33.4 | | | | |
| 21.112 | 4.20469 | 939 | 18.5 | | | | |
| 21.774 | 4.07839 | 1531 | 30.2 | | | | |
| 22.467 | 3.95423 | 1979 | 39.1 | | | | |
| 23.473 | 3.78686 | 1523 | 30.1 | | | | |
| 24.297 | 3.66028 | 955 | 18.9 | | | | |
| 24.676 | 3.60492 | 1653 | 32.7 | | | | |
| 25.446 | 3.49753 | 1489 | 29.4 | | | | |
| 27.125 | 3.28481 | 1402 | 27.7 | | | | |
| 28.025 | 3.18133 | 1073 | 21.2 | | | | |
| 29.209 | 3.05494 | 1049 | 20.7 | | | | |
| 30.175 | 2.95937 | 733 | 14.5 | | | | |
| 31.232 | 2.86158 | 769 | 15.2 | | | | |
| 34.073 | 2.62921 | 562 | 11.1 | | | | |
| 36.563 | 2.45565 | 601 | 11.9 | | | | |

FIG. 13

CRYSTAL FORM OF ETHYL (S)-3-(8-BROMO-1-METHYL-6-(PYRIDIN-2-YL)-4H-BENZO[F]IMIDAZO[1,2-A][1,4]DIAZEPIN-4-YL)PROPANOATE HYDROCHLORIDE

CROSS REFERENCE TO RELATED APPLICATION

This application claims the priority to Chinese PCT Application PCT/CN2019/074935 filed on Feb. 13, 2019 which claims priority of Chinese Patent Application No. 201810151979.0 filed on Feb. 13, 2018, the content of which is incorporated herein by reference.

TECHNICAL FIELD

The present invention relates to hydrochloride of benzodiazepine derivatives, and their crystal forms, preparation method and use thereof.

BACKGROUND OF THE INVENTION

Remimazolam (CNS 7056) is a new generation of benzodiazepine derivatives improved on the basis of midazolam. It has attracted attention due to its fast onset of action and fast recovery. With the deepening of research, the shortcomings of remimazolam gradually emerged. In the Phase II clinical trial of ICU sedation, Ono Company found that the hemodynamics of the patients was unstable after receiving remimazolam, and the plasma concentration in 10% of the patients was higher than the normal range (PAION AG Analyst call Oct. 14, 2014).

WO 0069836 disclosed remimazolam and pharmaceutically acceptable salt thereof, but did not disclose the preparation method of the pharmaceutically acceptable salt. CN 104059071 and CN 103221414 disclosed preparation methods and crystal forms of remimazolam besylate and p-toluenesulfonate. PCT/CN2015/084770 disclosed a series of methods for preparing benzodiazepine derivatives and their sulfonates. These derivatives have a good intravenous anesthesia effect. In the published references, the salt of these compounds is formed by employing an organic sulfonic acid (such as ethanesulfonic acid, benzenesulfonic acid, p-toluenesulfonic acid, etc.) with a basic group of the benzodiazepines to increase their solubility in water. However, employing an organic sulfonic acid to form a salt has the following disadvantages: it is necessary to use a corresponding alcohol as a solvent for the benzodiazepine derivative during the salification. If an organic sulfonic acid is employed, there is a possibility to form an organic sulfonate ester. For example, see the following reaction scheme:

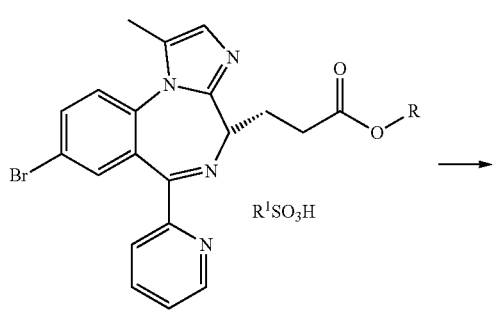

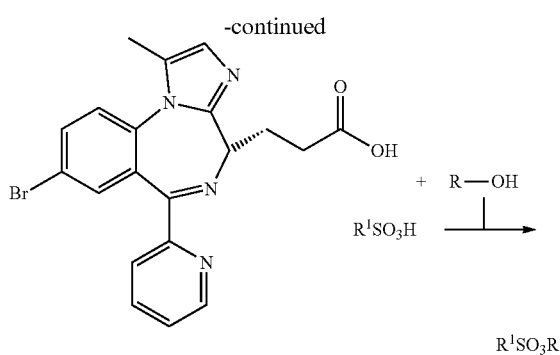

wherein R is methyl or ethyl; R' is methyl, ethyl, phenyl, 4-methylphenyl, 4-hydroxyphenyl and the like.

The organic sulfonate ester thus produced has a strong genotoxicity (ICH Harmonised Tripartite Guideline, Assessment and Control of DNA Reactive (Mutagenic) Impurities in Pharmaceuticals to Limit Potential Carcinogenic Risk, Current Step 4 version, 23 Jun. 2014). Therefore, these organic sulfonates of the benzodiazepine derivatives have the risk of forming potentially genotoxic substances during their production, storage and application. The genotoxic substances are characterized in that they may cause damage to human genetic materials at a very low concentration, and then may lead to gene mutations and promote tumorigenesis. Because of their strong toxicity, genotoxic substances pose a strong threat to the drug safety. In recent years, more and more serious medical accidents are occurred due to traces of genotoxic impurities found in the marketed drugs. Therefore, regulatory agencies in various countries, such as ICH, FDA, EMA, etc., have more specific requirements for genotoxic impurities, and more and more pharmaceutical companies are focusing on the control and testing of genotoxic impurities in the development of new drugs. In order to avoid the risk of genotoxicity caused by an organic sulfonate ester, it is preferable to replace the sulfonate with an acid radical with no or only a small risk of genotoxicity, such as Cl. However, there are multiple basic centers in the free base molecules of such benzodiazepine derivatives, using a general method—single amino group to form a salt with a strong acid-hydrochloric acid, which forms a mixture of single and multiple salts, making it difficult to obtain monohydrochloride, and leading to difficulty in crystallization, strong hygroscopicity and poor stability.

SUMMARY OF THE INVENTION

According to an aspect of the present invention, it provides a crystalline form of hydrochloride of a benzodiazepine derivative of Formula I or its ethanolate, Formula I

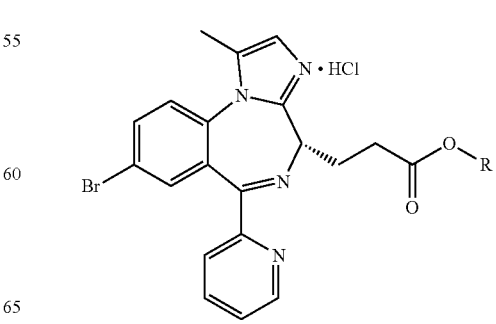

wherein R is methyl or ethyl; wherein when R is methyl, the crystal form has the following cell parameters: a=7.6929(6) Å, b=11.9174(10) Å, c=13.2096(11) Å, α=90°, β=96.904 (1°), γ=90°; and when R is ethyl, the crystal form has the following cell parameters: a=7.3774(1) Å, b=12.7332(2) Å, c=27.1779(4) Å, α=90°, β=90°, γ=90°.

In an embodiment according to this aspect, R is methyl, and its crystal form has a structure substantially as shown in FIG. 1, or may be characterized by one or more parameters substantially as shown in Tables 1-6. In another embodiment, R is ethyl, and its crystal form has a structure substantially as shown in FIG. 2, or may be characterized by one or more parameters substantially as shown in Tables 7-12.

In an embodiment according to this aspect, R is methyl, and the compound of Formula I has a content of chloride ion of 6.71-7.52% (w/w). In another embodiment, R is ethyl, and the compound of Formula I has a content of chloride ion of 6.51-7.31% (w/w).

In one embodiment, the crystal form of the compound of Formula I wherein R is methyl has an X-ray powder diffraction pattern with the following 2θ values measured by using CuKα radiation: about 6.81, 8.93, 13.39, 19.38, 21.23, 22.42, 24.20, 27.31±0.2 degrees. The X-ray powder diffraction pattern may also have the following 2θ values measured by using CuKα radiation: about 8.11, 9.86, 14.73, 17.47, 23.03, 25.94, 28.31±0.2 degrees. In addition, the crystal form has an X-ray powder diffraction pattern substantially as shown in FIG. 3.

In another embodiment, the crystal form of the compound of Formula I wherein R is methyl, has an X-ray powder diffraction pattern with the following 2θ values measured by using CuKα radiation: about 6.80, 8.93, 9.87, 13.37, 14.69, 19.36, 20.76, 21.25, 22.19, 22.38, 23.06, 24.21, 25.93, 27.73±0.2 degrees. The X-ray powder diffraction pattern may also have the following 2θ values measured by using CuKα radiation: about 16.14, 17.48, 20.02, 25.17, 26.36, 28.30, 34.13±0.2 degrees. In addition, the crystal form has an X-ray powder diffraction pattern substantially as shown in FIG. 4.

In an embodiment, the crystal form of the compound of Formula I wherein R is ethyl has an X-ray powder diffraction pattern with the following 2θ values measured by using CuKα radiation: about 6.87, 7.38, 9.53, 13.65, 18.71, 22.13, 22.67, 25.10, 27.25, 29.30±0.2 degrees. The X-ray powder diffraction pattern may also have the following 2θ values measured by using CuKα radiation: about 14.96, 15.43, 20.23, 20.67, 21.13, 23.52, 28.22, 31.26±0.2 degrees. In addition, the crystal form has an X-ray powder diffraction pattern substantially as shown in any one of FIGS. 5-8.

In an embodiment, the crystal form of the compound of Formula I wherein R is ethyl has an X-ray powder diffraction pattern with the following 2θ values measured by using CuKα radiation: about 7.41, 9.24, 12.71, 13.64, 15.06, 18.30, 18.72, 21.59, 22.18, 25.74±0.2 degrees. The X-ray powder diffraction pattern may also have the following 2θ values measured by using CuKα radiation: about 9.52, 11.69, 20.90, 22.60, 23.65, 24.26, 26.40, 28.43, 29.35±0.2 degrees. In addition, the crystal form has an X-ray powder diffraction pattern substantially as shown in FIG. 9.

In another embodiment, the crystal form of the compound of Formula I wherein R is ethyl has an X-ray powder diffraction pattern with the following 2θ values measured by using CuKα radiation: about 6.84, 7.37, 9.53, 13.66, 22.63, 25.57, 29.28, 31.26±0.2 degrees. The X-ray powder diffraction pattern may also have the following 2θ values measured by using CuKα radiation: about 15.43, 19.07, 22.16, 34.25±0.2 degrees. In addition, the crystal form has an X-ray powder diffraction pattern substantially as shown in any one of FIGS. 10-13.

According to another aspect of the present invention, it provides a method for preparing the above-mentioned crystal forms of the hydrochloride of the benzodiazepine derivative of Formula I according to the present invention, comprising the following steps: dissolving the free base of the benzodiazepine derivative of the following Formula II-1 or II-2 in an organic solvent 1, adding HCl donor A wherein [H+] is equimolar to the free base, to form a salt at a temperature of −20 to 60° C., preferably −10 to 30° C., after decolorizing the crude salt, crystallizing it in a crystallization solvent 1 at a temperature of −60 to 80° C., preferably −20 to 60° C., to obtain the crystal form of the hydrochloride of the benzodiazepine derivative of Formula I.

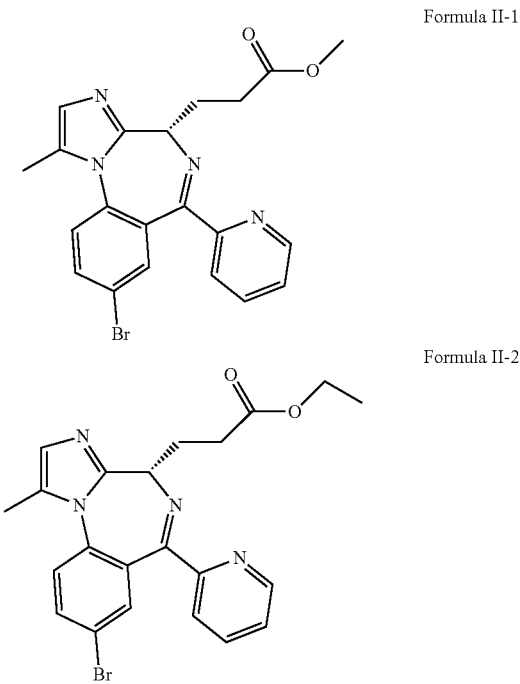

Formula II-1

Formula II-2

In an embodiment according to this aspect, the organic solvent 1 is an alcohol solvent, such as methanol, ethanol, n-propanol, isopropanol, n-butanol, isobutanol; an ester solvent, such as methyl acetate, ethyl acetate, propyl acetate, isopropyl acetate, butyl acetate; a ketone solvent, such as acetone and butanone; or a mixture thereof.

In an embodiment according to this aspect, the HCl donor A is an amino acid hydrochloride, such as glycine hydrochloride, alanine hydrochloride, valine hydrochloride; a HCl-anhydrous alcohol solution, that is, an alcohol solution of dry HCl, such as dry HCl-methanol solution, dry HCl-ethanol solution, dry HCl-isopropanol solution; or a solution B that can generate HCl, such as acetyl chloride-methanol solution, acetyl chloride-ethanol solution, propionyl chloride-ethanol solution, acetyl chloride-isopropanol solution.

In an embodiment according to this aspect, the HCl donor A is an amino acid hydrochloride, and the crystal form of the hydrochloride of the benzodiazepine derivative has an amount of amino acid of 0%-8% (w/w).

In an embodiment according to this aspect, the HCl donor A is a HCl-anhydrous alcohol solution or a solution B that can generate HCl, and the ratio of amount of substance (molar ratio) of the free base of the benzodiazepine derivative to the HCl donor A (calculated by [H⁺]) is 1:0.4-1; the HCl donor A is an amino acid hydrochloride, and the amount ratio (molar ratio) of the free base of the benzodiazepine derivative to the amino acid hydrochloride is 1:1-10.

In an embodiment according to this aspect, the crystallization solvent 1 comprises an alcohol solvent, such as methanol, ethanol, n-propanol, isopropanol, n-butanol, isobutanol; an ether solvent, such as ethyl ether, isopropyl ether, dioxane, methyl tert-butyl ether; an ester solvent, such as methyl acetate, ethyl acetate, propyl acetate, isopropyl acetate, butyl acetate; a ketone solvent, such as acetone and butanone; an alkane solvent, such as n-pentane, hexane, heptane, petroleum ether; a halogenated alkane, such as dichloromethane, chloroform, 1,2-dichloroethane; and a combination thereof.

According to another aspect of the present invention, it provides a pharmaceutical composition comprising the above-mentioned crystal form of the hydrochloride of the benzodiazepine derivative of Formula I according to the present invention, and a pharmaceutically acceptable excipient, carrier and/or other auxiliary materials.

The crystal form and the pharmaceutical composition according to the present invention may be used as intravenous anesthetics.

According to yet another aspect of the present invention, it provides a method of anesthesia, comprising intravenously administering an effective amount of the crystal form of the hydrochloride of the benzodiazepine derivative of Formula I according to the present invention, or a pharmaceutical composition comprising the crystal form to a subject in need thereof.

The crystal form of the hydrochloride of the benzodiazepine derivative provided by the present invention can not only improve the stability of the benzodiazepine derivative, but also eliminate the possibility of forming sulfonate ester impurities with strong genotoxicity during production and storage of the benzodiazepine derivative sulfonate, and has a more excellent anesthetic effect, which is more conducive to clinical use.

In addition, the present invention provides a hydrochloride of the benzodiazepine derivative of Formula I, which, compared to the corresponding sulfonate, 1) has good stability and is less prone to produce a hydrolysis product; 2) does not produce sulfonate ester impurities with strong genotoxicity during production or long-term storage; 3) has a shorter duration of anesthesia and a shorter interval of time to start walking after awakening, less individual differences, which is of great clinical significance.

The present invention will be described in more detail below with reference to the drawings.

DETAILED DESCRIPTION OF THE INVENTION

The present invention provides a crystal structure of a hydrochloride of a benzodiazepine derivative of the following general Formula I and its ethanolate,

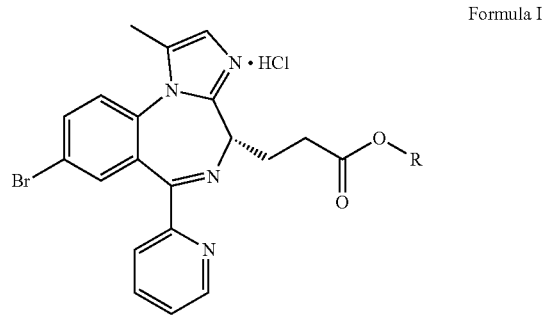

Formula I wherein R is methyl or ethyl.

Figure 1:
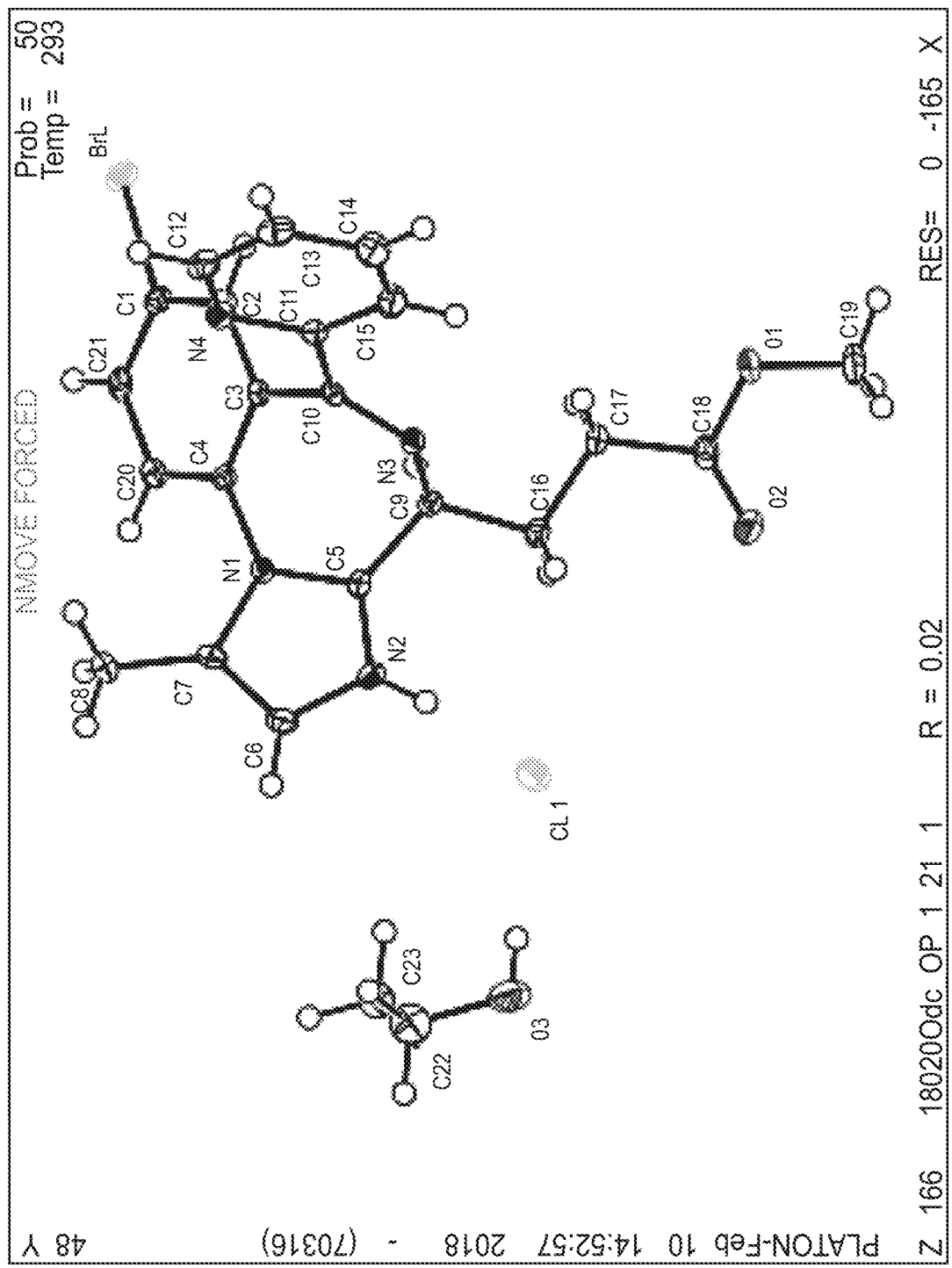
FIG. 1: The monocrystal molecular structure of an ethanolate of a compound of Formula I wherein R is methyl.

According to one embodiment of the present invention, when R is methyl, the crystal of the ethanolate of the benzodiazepine hydrochloride provided by the present invention has the following cell parameters: a=7.6929(6) Å, b=11.9174(10) Å, c=13.2096(11) Å, α=90°, β=96.904(1°), γ=90°. It may also be further characterized by its structure as shown in FIG. 1, the parameters as shown in Table 1, the structural coordinates as shown in Table 2, Table 3, and Table 4, and the bond lengths and angles as shown in Table 5 and Table 6.

Figure 2:
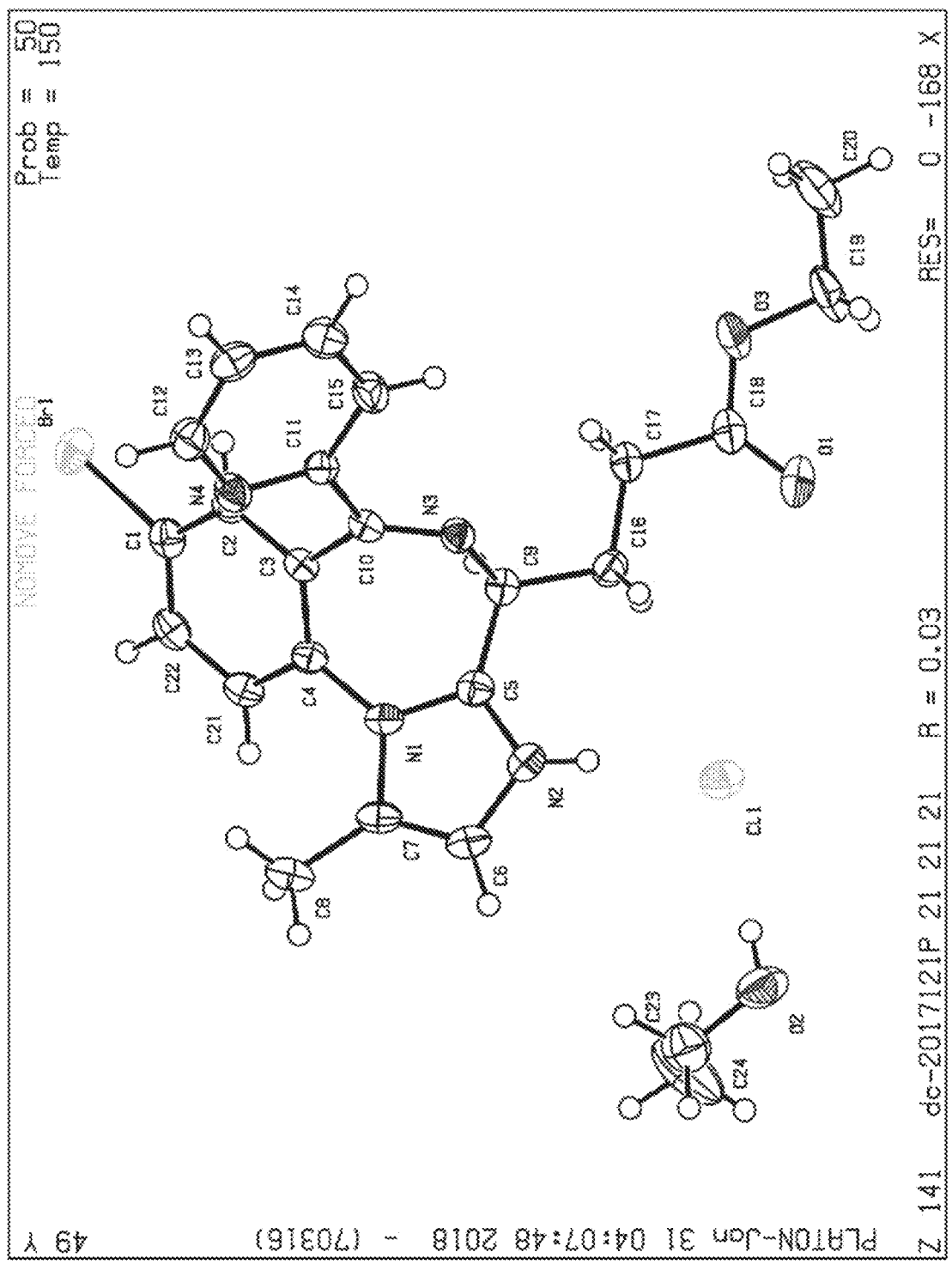
FIG. 2: The monocrystal molecular structure of an ethanolate of a compound of Formula I wherein R is ethyl.

According to one embodiment of the present invention, when R is ethyl, the crystal of the ethanolate of the benzodiazepine hydrochloride provided by the present invention has the following cell parameters: a=7.3774(1) Å, b=12.7332(2) Å, c=27.1779(4) Å, α=90°, β=90°, γ=90°. It may also be further characterized by its structure as shown in FIG. 2, the structural parameters as shown in Table 7, the structural coordinates as shown in Table 8, Table 9, and Table 10, and the bond lengths and angles as shown in Table 11 and Table 12.

According to an embodiment of the present invention, when R is methyl, the compound of Formula I has a content of chloride ion of 6.71-7.52% (w/w).

In an embodiment of the present invention, when R is ethyl, the compound of Formula I has a content of chloride ion of 6.51-7.31% (w/w).

The hydrochloride of the benzodiazepine derivative provided by the present invention is a crystalline salt, and their crystal structures and X-ray powder diffraction data and patterns are also provided.

Figure 3:
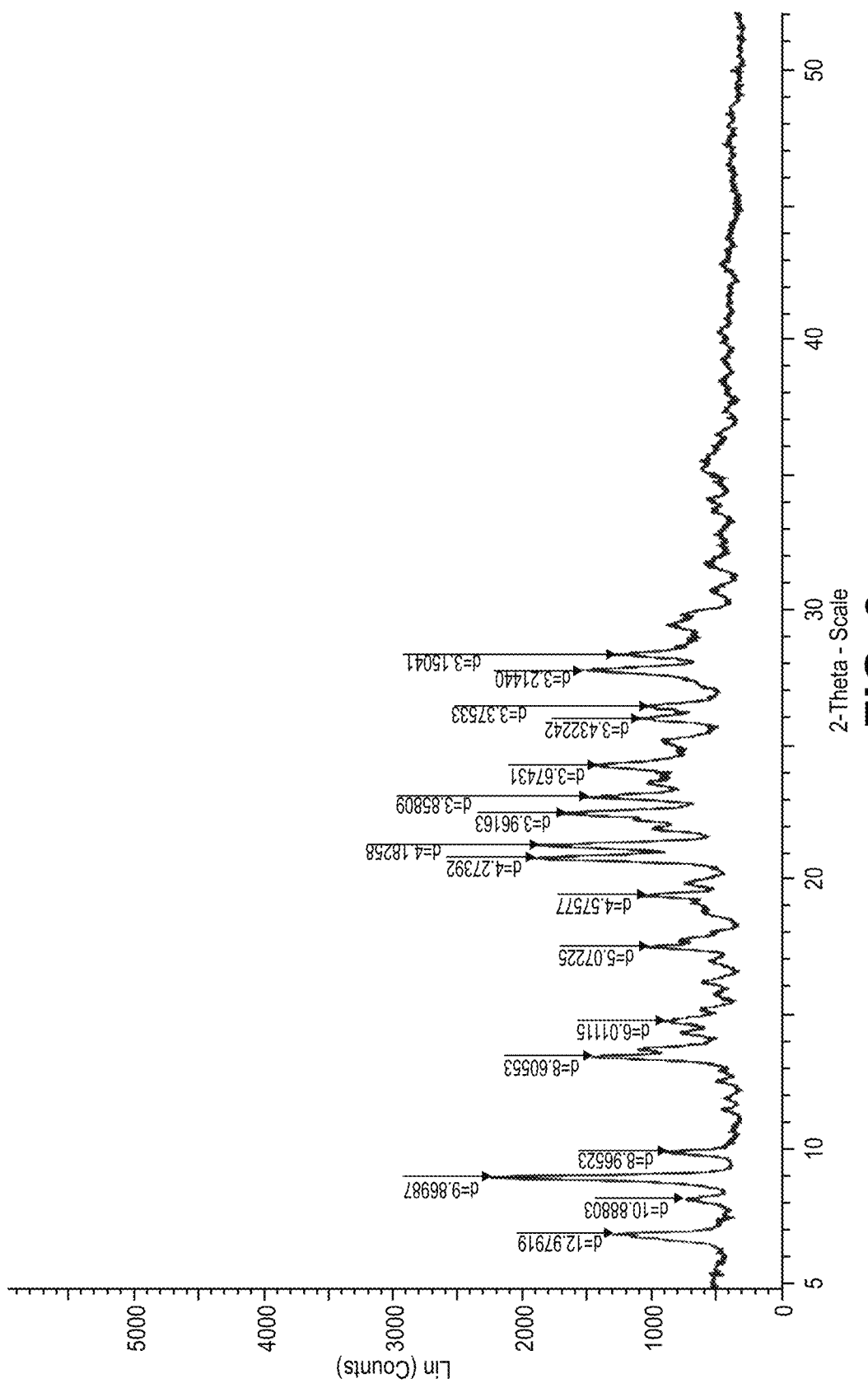
FIG. 3: An X-ray powder diffraction pattern of the crystal of a compound of Formula I wherein R=CH₃ (CNS-7056A2017120401)

According to an embodiment of the present invention, R is methyl, and it has an X-ray powder diffraction pattern expressed in 2θ degrees by using Cu-Kα radiation with characteristic absorption at about 6.81, 8.93, 13.39, 19.38, 21.23, 22.42, 24.20, 27.31±0.2, and can be further characterized by an X-ray powder diffraction pattern at 2θ of about 8.11, 9.86, 14.73, 17.47, 23.03, 25.94, 28.31±0.2 degrees, or the X-ray powder diffraction pattern as shown in FIG. 3.

Figure 4:
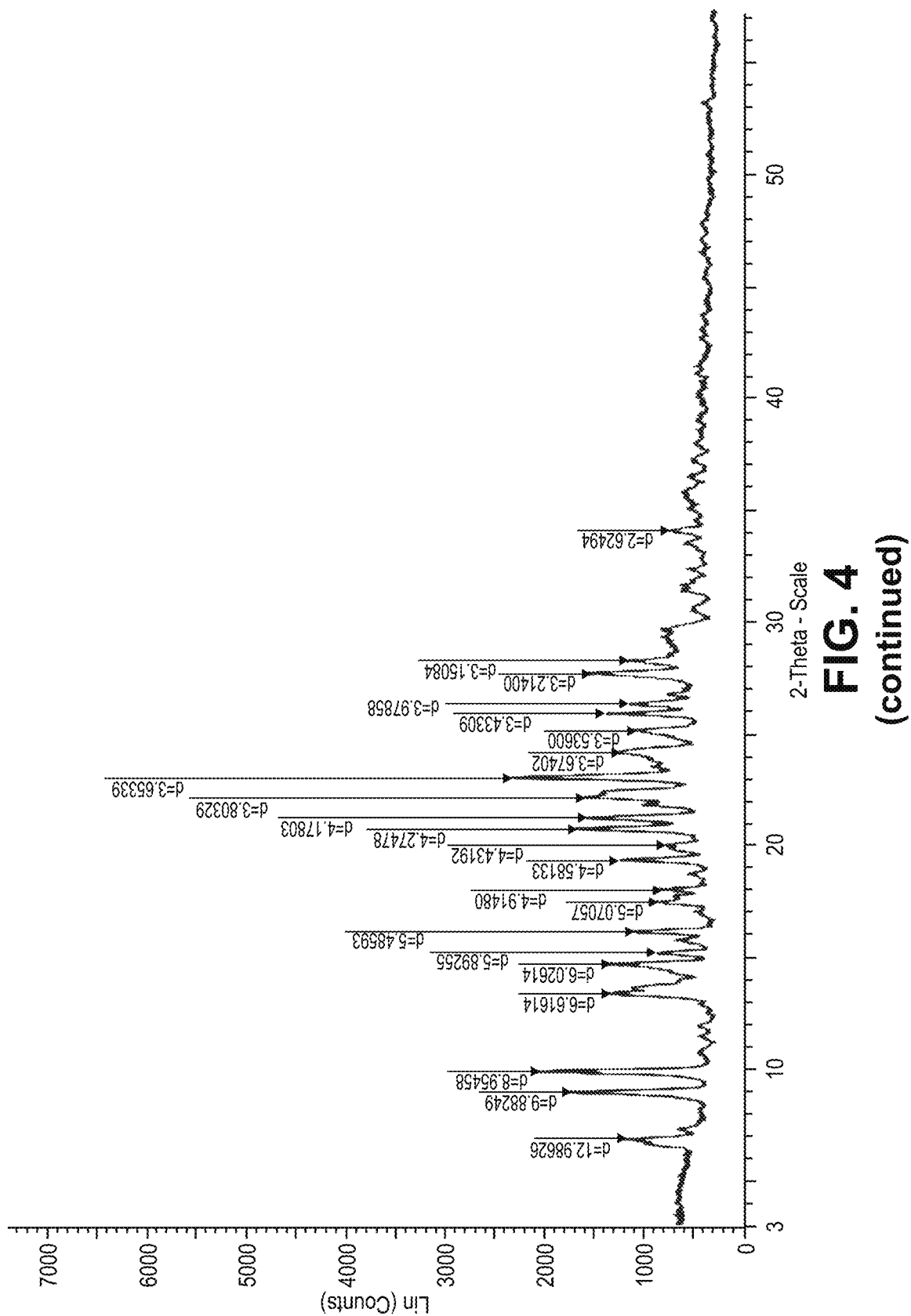
FIG. 4: An X-ray powder diffraction pattern of the crystal of a compound of Formula I wherein R=CH₃ (CNS-7056AG20171225)

According to an embodiment of the present invention, R is methyl, and it has an X-ray powder diffraction pattern expressed in 2θ degrees by using Cu-Kα radiation with characteristic absorption at about 6.80, 8.93, 9.87, 13.37, 14.69, 19.36, 20.76, 21.25, 22.19, 22.38, 23.06, 24.21, 25.93, 27.73±0.2, and can be further characterized by an X-ray powder diffraction pattern at 2θ of about 16.14, 17.48, 20.02, 25.17, 26.36, 28.30, 34.13±0.2 degrees, or the X-ray powder diffraction pattern as shown in FIG. 4. According to an embodiment of the present invention, R is ethyl, and it has an X-ray powder diffraction pattern expressed in 2θ degrees by using Cu-Kα radiation with characteristic absorption at about 6.87, 7.38, 9.53, 13.65, 18.71, 22.13, 22.67, 25.10, 27.25, 29.30±0.2, and can be further characterized by an X-ray powder diffraction pattern at 2θ of about 14.96, 15.43, 20.23, 20.67, 21.13, 23.52, 28.22, 31.26±0.2 degrees, or the X-ray powder diffraction patterns as shown in FIGS. 5-8.

Figure 9:
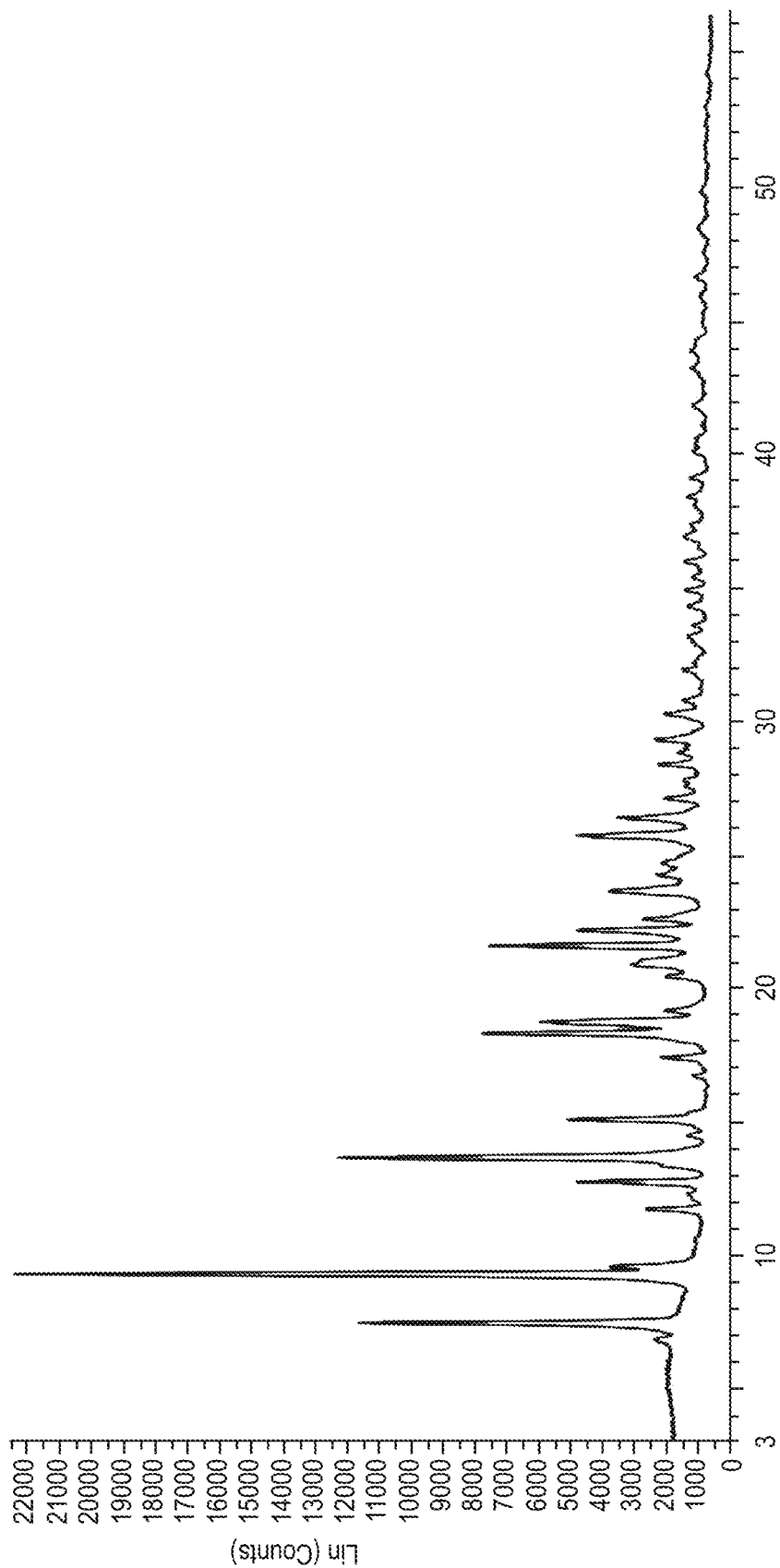
FIG. 9: An X-ray powder diffraction pattern of the crystal of a compound of Formula I wherein R=CH₂CH₃ (EL-001A20180130)

According to an embodiment of the present invention, R is ethyl, and it has an X-ray powder diffraction pattern expressed in 2θ degrees by using Cu-Kα radiation with characteristic absorption at about 7.41, 9.24, 12.71, 13.64, 15.06, 18.30, 18.72, 21.59, 22.18, 25.74±0.2, and can be further characterized by an X-ray powder diffraction pattern at 2θ of about 9.52, 11.69, 20.90, 22.60, 23.65, 24.26, 26.40, 28.43, 29.35±0.2 degrees, or the X-ray powder diffraction pattern as shown in FIG. 9.

According to an embodiment of the present invention, R is ethyl, and it has an X-ray powder diffraction pattern expressed in 2θ degrees by using Cu-Kα radiation with characteristic absorption at about 6.84, 7.37, 9.53, 13.66, 22.63, 25.57, 29.28, 31.26±0.2, and can be further characterized by an X-ray powder diffraction pattern at 2θ of about 15.43, 19.07, 22.16, 34.25±0.2 degrees, or the X-ray powder diffraction patterns as shown in FIGS. 10-13.

According to a second aspect of the present invention, it provides a method for preparing the hydrochloride of the benzodiazepine derivative and its crystal form: dissolving the free base of the benzodiazepine derivative in an organic solvent 1; adding HCl donor A equimolar to the free base of the benzodiazepine derivative, to form a salt at −20-60° C. to obtain a crude product; and after decolorizing, crystallizing the crude product in a crystallization solvent 1 at −60-80° C. to obtain hydrochloride of the benzodiazepine derivative.

According to an embodiment of the present invention, the organic solvent 1 is an alcohol solvent (such as methanol, ethanol, n-propanol, isopropanol, n-butanol, isobutanol, etc.), an ester solvent (such as methyl acetate, ethyl acetate, propyl acetate, isopropyl acetate, butyl acetate, etc.), a ketone solvent (such as acetone, butanone, etc.), or mixtures thereof.

According to an embodiment of the present invention, the HCl donor A is an amino acid hydrochloride (such as glycine hydrochloride, alanine hydrochloride, valine hydrochloride, etc.), a HCl-anhydrous alcohol solution (i.e., alcohol solution of dry HCl gas, such as dry HCl-methanol solution, dry HCl-ethanol solution), a solution B that can generate HCl (such as acetyl chloride-methanol solution, acetyl chloride-ethanol solution, etc.).

According to an embodiment of the present invention, when the HCl donor A is an amino acid hydrochloride, the hydrochloride of the benzodiazepine derivative has an amount of amino acid of 0%-8% (w/w).

According to an embodiment of the present invention, when the HCl donor A is an amino acid hydrochloride, the ratio of amount of substance of the benzodiazepine derivative (calculated by free base) to the amino acid hydrochloride is 1:1-10; and when the HCl donor A is a HCl-anhydrous alcohol solution or a solution B that can generate HCl, the amount ratio of the benzodiazepine derivative (calculated by free base) to acid (calculated by HCl) is 1:0.4-1.

According to an embodiment of the present invention, the temperature for forming a salt is −20 to 60° C., preferably −10 to 30° C.; and the crystallization temperature is −60-80° C., preferably −20-60° C.

According to an embodiment of the present invention, the crystallization solvent 1 comprises an alcohol solvent (such as methanol, ethanol, n-propanol, isopropanol, n-butanol, isobutanol, etc.), an ether solvent (such as diethyl ether, isopropyl ether, dioxane, methyl tert-butyl ether, isopropyl ether, etc.), an ester solvent (such as methyl acetate, ethyl acetate, propyl acetate, isopropyl acetate, butyl acetate, etc.), a ketone solvent (such as acetone, butanone, etc.), an alkane solvent (such as pentane, hexane, heptane, petroleum ether, etc.), a halogenated alkane (such as dichloromethane, chloroform, 1,2-dichloroethane, etc.) and combinations thereof.

According to a third aspect of the present invention, it provides the hydrochloride of the benzodiazepine derivative and the pharmaceutical composition of the present invention, which can be used as intravenous anesthetics.

The pharmaceutical composition comprises the above-mentioned crystal form of the hydrochloride of the benzodiazepine derivative of Formula I according to the present invention, and optionally a pharmaceutically acceptable excipient, carrier and/or other auxiliary materials. The excipient and/or carrier include, for example, one or more of mannitol, sorbitol, xylitol, sucrose, lactose, glucose, dextrin, maltose, maltitol, maltodextrin, erythritol, trehalose, calcium gluconate, calcium sulfate, sodium chloride, glycine, hydrolyzed gelatin, human albumin, etc. The composition may optionally include other auxiliary materials, such as a pH adjusting agent, stabilizer, analgesic, bacteriostatic agent, and the like. The pH adjusting agent includes, for example, one or more of hydrochloric acid, sulfuric acid, phosphoric acid, citric acid, acetic acid, sodium dihydrogen phosphate, potassium dihydrogen phosphate, ammonium dihydrogen phosphate, disodium hydrogen phosphate, dipotassium hydrogen phosphate, diammonium hydrogen phosphate, sodium phosphate, potassium phosphate, ammonium phosphate, sodium bisulfate, potassium bisulfate, ammonium bisulfate, sodium bicarbonate, potassium bicarbonate, sodium carbonate, potassium carbonate, sodium hydroxide, potassium hydroxide, ammonia water, citric acid, sodium dihydrogen citrate, potassium dihydrogen citrate, ammonium dihydrogen citrate, disodium hydrogen citrate, dipotassium hydrogen citrate, diammonium hydrogen citrate, potassium sodium hydrogen citrate, sodium citrate, potassium citrate, ammonium citrate, lactic acid, sodium lactate, potassium lactate, ammonium lactate, malic acid, sodium malate, potassium malate, malic acid, sodium hydrogen malate, potassium hydrogen malate, ammonium hydrogen malate, potassium sodium malate, tartaric acid, sodium hydrogen tartrate, potassium hydrogen tartrate, ammonium hydrogen tartrate, potassium sodium tartrate, vitamin C, sodium vitamin C, alginic acid, sodium alginate, succinic acid, sodium succinate, potassium succinate, ammonium succinate, sodium hydrogen succinate, potassium hydrogen succinate, ammonium hydrogen succinate, potassium sodium succinate, acetic acid, sodium acetate, potassium acetate, ammonium acetate, amino acids and their salts. The stabilizer includes, for example, one or more of sodium bisulfite, sodium metabisulfite, sodium sulfite, sodium thiosulfate, vitamin C, sodium thioglycolate, glycine, cysteine, disodium edetate, sodium calcium edetate, etc. The analgesic include, for example: one or more of benzyl alcohol, 1,1,1-trichloro-2-methyl-2-propanol and the like. The bacteriostatic agent includes, for example, one or more of benzyl alcohol, 1,1,1-trichloro-2-methyl-2-propanol, benzoic acid and its salts, sorbic acid and its salts, parabens and the like.

According to a fourth aspect of the present invention, it provides a method of anesthesia, comprising intravenously administering a certain dose of the hydrochloride of the benzodiazepine derivative and the pharmaceutical composition of the present invention to a patient.

According to a fifth aspect of the present invention, it provides the use of the hydrochloride of the benzodiazepine derivative of the present invention in the preparation of intravenous anesthetics.

In order to better illustrate the objective and technical solution of the present invention, examples of the present invention are described in detail below. It should be noted that the following examples are only used to further illustrate the present invention, and cannot be understood as limiting the scope of protection of the present invention. Some non-essential improvements and adjustments made by those skilled in the art based on the above content of the present invention fall into the protection scope of the present invention.

The preparation of the free base of the benzodiazepine derivative (Formula II-1, Formula II-2) involved in the preparation method according to the present invention is disclosed in PCT/CN2015/084770 and WO0069836, which are incorporated herein as a reference in their entirety.

Formula II-1

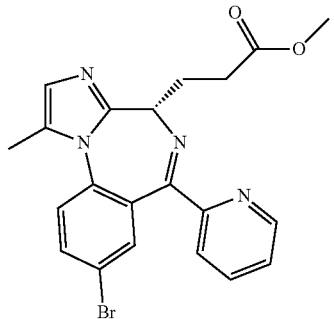

Formula II-2

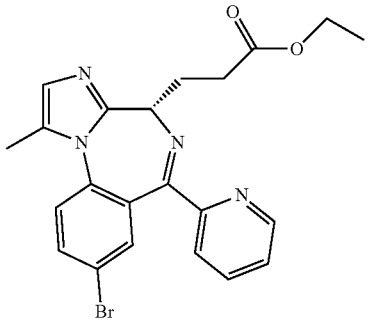

Test Instruments Used in the Experiment

X-ray powder diffraction pattern: Instrument model: Bruker D8 FOCUS X-ray powder diffractometer; X-ray: Cu target; Scanning method: θ/2θ; Scanning range: 3-60°; Voltage: 40 KV; Current: 40 mA.

A. Preparation of the Hydrochloride of the Compound of Formula II-1 (the Compound of Formula I Wherein R is Methyl)

A-1: Use of a HCl-Anhydrous Alcohol Solution as HCl Donor A

Example 1: Using a HCl-Anhydrous Methanol Solution

The compound of Formula II-1 (1.8 g, 4 mmol) was dissolved in anhydrous methanol (6 ml) at 13° C., and then 1.57 g anhydrous methanol-HCl (HCl content of 9.29%) (with HCl molar quantity of 4 mmol) was added dropwise thereto. The mixture reacted for 0.5 h, then MTBE (54 ml) was added dropwise and reacted for another 0.5 h. The reaction mixture was filtered, and the filter cake was dissolved in 30 ml of anhydrous methanol, decolorized at 50° C. for 0.5 h, and then filtered. The filtrate was concentrated, and the residue was dissolved in anhydrous methanol (14 ml) at 50° C. Methyl tert-butyl ether (7 ml) was added dropwise. The solution became turbid, and was stirred for 0.5 h. MTBE (98 ml) was added dropwise. Then, the solution was cooled to −10° C. and stirred for 1 hour and filtered. The filter cake was subjected to slurrying with ether (30 ml) for 1.5 h, and then filtered. The filter cake was dried to obtain 1.62 g of a white solid, with a yield of 90%, purity: 99.57%, m.p: 173-175° C. The theoretical value of chloride ion content was 7.45% (w/w), and the measured value was 7.42% (w/w). See FIG. 3 for the X-ray powder diffraction pattern.

A-2: Use of Amino Acid Hydrochloride as HCl Donor A

Example 2: Using Glycine Hydrochloride

Glycine hydrochloride (2.46 g, 22 mmol) was added in anhydrous methanol (50 ml) at 60° C. An anhydrous methanol solution (15 ml) containing the compound of Formula II-1 (5 g, 11 mmol) was added dropwise to the above mixture within 5 min, and allowed to react for 0.5 h. The reaction mixture was cooled to −20° C. and maintained at this temperature overnight, and then filtered. The filtrate was concentrated, and the residue was dissolved in anhydrous methanol (50 ml), decolorized at 55-60° C. for 0.5 h, and then filtered. The filtrate was concentrated, and the residue was dissolved in anhydrous methanol (20 ml) at 60° C. Methyl tert-butyl ether (140 ml) was added dropwise thereto. Then, it was cooled to room temperature and stirred overnight, and then filtered. The obtained solid was dried to obtain the target product. The theoretical value of chloride ion content was 7.45% (w/w), and the measured value was 7.38% (w/w). See FIG. 4 for the X-ray powder diffraction pattern.

Example 3: Using Valine Hydrochloride

With reference to the operation of Example 2, the target compound was prepared with the compound of Formula II-1 and valine hydrochloride as starting materials (with a molar ratio of 1:1.5). The theoretical value of chloride ion content was 7.45% (w/w), and the measured value was 6.94% (w/w).

Example 4: Using Alanine Hydrochloride

With reference to the operation of Example 2, the target compound was prepared with the compound of Formula II-1 and alanine hydrochloride as starting materials (with a molar ratio of 1:3). The theoretical value of chloride ion content was 7.45% (w/w), and the measured value was 6.81% (w/w).

A-3: Use of a Solution B that can Generate HCl as HCl Donor A

Example 5: Using Acetyl Chloride-Anhydrous Methanol Solution

With reference to the operation of Example 1, the target compound was prepared by crystallizing at 20° C., with the compound of Formula II-1 and acetyl chloride-anhydrous methanol solution as starting materials (with a molar ratio of acetyl chloride to the compound of Formula II-1 of 1:1). Theoretical value of chloride ion content was 7.45% (w/w), and the measured value was 7.52% (w/w).

Example 6: Preparation and Structural Characterization of a Single Crystal of an Ethanolate of a Compound of Formula I Wherein R is Methyl The compound of Formula I prepared in Example 1 was recrystallized with ethanol and methyl tert-butyl ether, and allowed to stand at room temperature for 4 days. The crystals were then collected. The obtained crystal was subjected to an X-ray single crystal diffraction experiment, and its crystal parameters are shown in Tables 1-6 below.

TABLE 1

Data and structure refinement data of the crystal of the ethanolate of the compound of Formula I wherein R is methyl

| Bond precision: | C—C = 0.0032 A | Wavelength = 0.71073 |
|---|---|---|
| Cell: | a = 7.6929 (6) | b = 11.9174 (10)  c = 13.2096 (11) |
| | alpha = 90 | beta = 96.904 (1)   gamma = 90 |
| Temperature: | 293 K | |

| | Calculated | Reported |
|---|---|---|
| Volume | 1202.27 (17) | 1202.27 (17) |
| Space group | P 21 | P 1 21 1 |
| Hall group | P 2yb | P 2yb |
| Moiety formula | C21 H20 Br N4 O2, C2 H6 O, Cl | C21 H20 Br N4 O2, Cl, C2 H6 O |
| Sum formula | C23 H26 Br Cl N4 O3 | C23 H26 Br Cl N4 O3 |
| Mr | 521.83 | 1.441 |

TABLE 1-continued

Data and structure refinement data of the crystal of the ethanolate of the compound of Formula I wherein R is methyl

| Dx, b cm-3 | 1.441 | 1.441 |
|---|---|---|
| Z | 2 | 2 |
| Mu (mm-1) | 1.852 | 1.852 |
| F000 | 536.0 | 536.0 |
| F000' | 535.91 | |
| H, k, lmax | 10, 15, 17 | 10, 15, 17 |
| Nref | 5607 (2937) | 4078 |
| Tmin, Tmax | | 0.565, 0.746 |
| Tmin' | | |

| Correction method = # Reported T Limits: Tmin = 0.565 Tmax = 0.746 |
|---|
| AbsCorr = MULTI-SCAN |
| Data Completeness = 1.39/0.73     Theta(max) = 27.651 |
| R(reflections) = 0.0204 (3828)    wR2 (reflections) = 0.0473 (4078) |
| S = 0.856     Npar = 293 |

TABLE 2

Non-hydrogen atomic coordinates ($\times 10^4$) and equivalent isotropic shift parameter ($Å^2 \times 10^3$) data of the ethanolate of the compound of Formula I wherein R is methyl

| No. of Atom | x | Y | z | U(eq) |
|---|---|---|---|---|
| Br(1) | −4202(1) | 8268(1) | 6312(1) | 20(1) |
| O(1) | 1797(2) | 1562(2) | 6318(1) | 24(1) |
| O(2) | 3608(2) | 1616(2) | 7788(1) | 24(1) |
| N(1) | 3120(2) | 7198(2) | 8336(1) | 11(1) |
| N(2) | 5345(3) | 6118(2) | 8788(1) | 14(1) |
| N(3) | 2920(3) | 5605(2) | 6571(1) | 12(1) |
| N(4) | 2033(3) | 7931(2) | 4955(1) | 16(1) |
| C(1) | −1864(3) | 8033(2) | 6918(2) | 15(1) |
| C(2) | −744(3) | 7443(2) | 6369(2) | 15(1) |
| C(3) | 940(3) | 7172(2) | 6826(2) | 12(1) |
| C(4) | 1444(3) | 7520(2) | 7839(2) | 12(1) |
| C(5) | 3750(3) | 6139(2) | 8272(2) | 12(1) |
| C(6) | 5737(3) | 7165(2) | 9197(2) | 17(1) |
| C(7) | 4366(3) | 7865(2) | 8929(2) | 14(1) |
| C(8) | 4159(3) | 9076(2) | 9132(2) | 19(1) |
| C(9) | 2771(3) | 5267(2) | 7635(2) | 12(1) |
| C(10) | 2080(3) | 6484(2) | 6240(2) | 12(1) |
| C(11) | 2264(3) | 6836(2) | 5168(2) | 13(1) |
| C(12) | 2297(3) | 8259(3) | 4006(2) | 19(1) |
| C(13) | 2764(3) | 7536(2) | 3271(2) | 20(1) |
| C(14) | 2999(3) | 6408(2) | 3507(2) | 22(1) |
| C(15) | 2745(3) | 6053(2) | 4475(2) | 19(1) |
| C(16) | 3417(3) | 4067(2) | 7808(2) | 14(1) |
| C(17) | 2268(3) | 3324(3) | 7070(2) | 20(1) |
| C(18) | 2680(3) | 2085(2) | 7127(2) | 17(1) |
| C(19) | 1984(4) | 359(2) | 6277(3) | 29(1) |
| C(20) | 324(3) | 8166(2) | 8354(2) | 15(1) |
| C(21) | −1338(3) | 8426(2) | 7891(2) | 16(1) |
| Cl(1) | 8473(1) | 4573(1) | 8670(1) | 25(1) |
| O(3) | 11847(2) | 5057(2) | 10155(1) | 30(1) |
| C(22) | 11733(4) | 6161(3) | 10571(2) | 29(1) |
| C(23) | 10127(4) | 6328(3) | 11098(2) | 27(1) |

Note:
U(eq) is defined as one third of the trace of the orthogonalized $U^{ij}$ tensor.

TABLE 3

Non-hydrogen atom anisotropic shift parameter ($Å^2 \times 10^3$) data of the ethanolate of the compound of Formula I wherein R is methyl

| No. of Atom | $U^{11}$ | $U^{22}$ | $U^{33}$ | $U^{23}$ | $U^{13}$ | $U^{12}$ |
|---|---|---|---|---|---|---|
| Br(1) | 10(1) | 18(1) | 30(1) | 5(1) | −2(1) | 1(1) |
| O(1) | 33(1) | 10(1) | 28(1) | −4(1) | −4(1) | 2(1) |
| O(2) | 25(1) | 15(1) | 30(1) | 4(1) | −2(1) | 1(1) |
| N(1) | 11(1) | 10(1) | 12(1) | −1(1) | 2(1) | 0(1) |
| N(2) | 12(1) | 14(1) | 16(1) | 2(1) | 0(1) | 3(1) |

TABLE 3-continued

Non-hydrogen atom anisotropic shift parameter (Å2 × 10³) data of the ethanolate of the compound of Formula I wherein R is methyl

| No. of Atom | $U^{11}$ | $U^{22}$ | $U^{33}$ | $U^{23}$ | $U^{13}$ | $U^{12}$ |
|---|---|---|---|---|---|---|
| N(3) | 14(1) | 10(1) | 12(1) | 1(1) | 1(1) | −1(1) |
| N(4) | 17(1) | 15(1) | 16(1) | 2(1) | −1(1) | −1(1) |
| C(1) | 9(1) | 14(2) | 22(1) | 2(1) | 0(1) | 0(1) |
| C(2) | 16(1) | 11(1) | 16(1) | 1(1) | −1(1) | −1(1) |
| C(3) | 13(1) | 8(1) | 14(1) | 0(1) | 1(1) | −1(1) |
| C(4) | 10(1) | 10(1) | 14(1) | 1(1) | 1(1) | 0(1) |
| C(5) | 13(1) | 10(1) | 12(1) | 1(1) | 3(1) | 1(1) |
| C(6) | 16(1) | 18(1) | 15(1) | 0(1) | −2(1) | −4(1) |
| C(7) | 14(1) | 16(1) | 10(1) | −1(1) | 0(1) | −2(1) |
| C(8) | 20(1) | 13(1) | 22(1) | −3(1) | −1(1) | −2(1) |
| C(9) | 14(1) | 11(1) | 12(1) | 1(1) | 1(1) | 1(1) |
| C(10) | 12(1) | 10(1) | 14(1) | −1(1) | −1(1) | −4(1) |
| C(11) | 12(1) | 13(1) | 13(1) | 0(1) | −1(1) | 0(1) |
| C(12) | 19(1) | 18(1) | 21(1) | 9(1) | −1(1) | −4(2) |
| C(13) | 19(1) | 26(1) | 14(1) | 6(1) | 2(1) | −2(1) |
| C(14) | 26(1) | 23(1) | 16(1) | −2(1) | 4(1) | 3(1) |
| C(15) | 24(1) | 16(1) | 18(1) | 1(1) | 2(1) | 3(1) |
| C(16) | 16(1) | 11(1) | 16(1) | 3(1) | 1(1) | 1(1) |
| C(17) | 25(1) | 9(1) | 25(1) | 0(1) | −5(1) | 3(1) |
| C(18) | 16(1) | 11(1) | 24(1) | 1(1) | 5(1) | −2(1) |
| C(19) | 31(2) | 11(1) | 45(2) | −5(1) | −1(1) | 3(1) |
| C(20) | 17(1) | 12(1) | 15(1) | −1(1) | 3(1) | −2(1) |
| C(21) | 14(1) | 11(1) | 23(1) | −2(1) | 7(1) | 2(1) |
| Cl(1) | 16(1) | 26(1) | 32(1) | −12(1) | −1(1) | 3(1) |
| O(3) | 22(1) | 40(1) | 26(1) | −5(1) | −3(1) | 9(1) |
| C(22) | 34(2) | 31(2) | 22(1) | 2(1) | 7(1) | −3(1) |
| C(23) | 27(1) | 26(2) | 27(1) | −3(1) | 1(1) | 2(1) |

TABLE 4

Hydrogen atomic coordinates (×10⁴) and equivalent isotropic shift parameter (AÅ2 × 10³) data of the ethanolate of the compound of Formula I wherein R is methyl

| No. of hydrogen atom | x | Y | z | U(eq) |
|---|---|---|---|---|
| H(2) | 6024 | 5542 | 8856 | 17 |
| H(2A) | −1108 | 7227 | 5701 | 18 |
| H(6) | 6775 | 7361 | 9593 | 20 |
| H(8A) | 3702 | 9449 | 8512 | 28 |
| H(8B) | 5276 | 9392 | 9382 | 28 |
| H(8C) | 3364 | 9174 | 9632 | 28 |
| H(9) | 1536 | 5300 | 7748 | 15 |
| H(12) | 2155 | 9015 | 3840 | 23 |
| H(13) | 2919 | 7800 | 2625 | 24 |
| H(14) | 3320 | 5903 | 3026 | 26 |
| H(15) | 2893 | 5302 | 4658 | 23 |
| H(16A) | 4631 | 4008 | 7684 | 17 |
| H(16B) | 3331 | 3840 | 8506 | 17 |
| H(17A) | 1060 | 3427 | 7193 | 24 |
| H(17B) | 2364 | 3580 | 6382 | 24 |
| H(19A) | 1305 | 76 | 5673 | 44 |
| H(19B) | 1577 | 28 | 6868 | 44 |
| H(19C) | 3194 | 171 | 6262 | 44 |
| H(20) | 693 | 8423 | 9010 | 18 |
| H(21) | −2090 | 8859 | 8230 | 19 |
| H(3) | 10946 | 4916 | 9780 | 45 |
| H(22A) | 11727 | 6706 | 10026 | 35 |
| H(22B) | 12763 | 6299 | 11054 | 35 |
| H(23A) | 9102 | 6175 | 10629 | 40 |

TABLE 4-continued

Hydrogen atomic coordinates (×10⁴) and equivalent isotropic shift parameter (AÅ2 × 10³) data of the ethanolate of the compound of Formula I wherein R is methyl

| No. of hydrogen atom | x | Y | z | U(eq) |
|---|---|---|---|---|
| H(23B) | 10090 | 7089 | 11333 | 40 |
| H(23C) | 10164 | 5827 | 11669 | 40 |

TABLE 5

Bond length (Å) and bond angle (°) data of the ethanolate of the compound of Formula I wherein R is methyl

| Bond | Bond length (bond angle °) | Bond | Bond length Å (bond angle °) |
|---|---|---|---|
| Br(1)—C(1) | 1.899(2) | N(1)—C(5) | 1.359(3) |
| O(1)—C(18) | 1.348(3) | N(1)—C(7) | 1.408(3) |
| O(1)—C(19) | 1.443(3) | N(2)—C(5) | 1.330(3) |
| O(2)—C(18) | 1.198(3) | N(2)—C(6) | 1.379(3) |
| N(1)—C(4) | 1.427(3) | N(3)—C(9) | 1.480(3) |
| N(3)—C(10) | 1.281(3) | C(2)—C(3) | 1.400(3) |
| N(4)—C(11) | 1.342(3) | C(3)—C(4) | 1.410(3) |
| N(4)—C(12) | 1.352(3) | C(3)—C(10) | 1.484(3) |
| C(1)—C(2) | 1.382(3) | C(4)—C(20) | 1.393(3) |
| C(1)—C(21) | 1.383(3) | C(5)—C(9) | 1.484(3) |
| C(6)—C(7) | 1.358(4) | C(12)—C(13) | 1.379(4) |
| C(7)—C(8) | 1.481(4) | C(13)—C(14) | 1.386(4) |
| C(9)—C(16) | 1.522(3) | C(14)—C(15) | 1.383(3) |
| C(10)—C(11) | 1.498(3) | C(16)—C(17) | 1.520(3) |
| C(11)—C(15) | 1.390(3) | C(17)—C(18) | 1.510(4) |
| C(20)—C(21) | 1.385(3) | C(18)—O(1)—C(19) | 116.5(2) |
| O(3)—C(22) | 1.432(4) | C(5)—N(1)—C(4) | 122.0(2) |
| C(22)—C(23) | 1.502(4) | C(5)—N(1)—C(7) | 109.57(19) |
| C(7)—N(1)—C(4) | 128.4(2) | C(2)—C(1)—C(21) | 121.9(2) |
| C(5)—N(2)—C(6) | 109.2(2) | C(21)—C(1)—Br(1) | 119.90(17) |
| C(10)—N(3)—C(9) | 117.0(2) | C(1)—C(2)—C(3) | 119.7(2) |
| C(11)—N(4)—C(12) | 116.5(2) | C(2)—C(3)—C(4) | 118.4(2) |
| C(2)—C(1)—Br(1) | 118.20(17) | C(2)—C(3)—C(10) | 118.5(2) |
| C(4)—C(3)—C(10) | 123.0(2) | N(2)—C(5)—N(1) | 107.4(2) |
| C(3)—C(4)—N(1) | 119.2(2) | N(2)—C(5)—C(9) | 130.7(2) |
| C(20)—C(4)—N(1) | 120.1(2) | C(7)—C(6)—N(2) | 109.1(2) |
| C(20)—C(4)—C(3) | 120.7(2) | N(1)—C(7)—C(8) | 124.7(2) |
| N(1)—C(5)—C(9) | 121.7(2) | C(6)—C(7)—N(1) | 104.7(2) |
| C(6)—C(7)—C(8) | 130.4(2) | N(3)—C(10)—C(11) | 116.8(2) |
| N(3)—C(9)—C(5) | 104.79(18) | C(3)—C(10)—C(11) | 117.8(2) |
| N(3)—C(9)—C(16) | 109.69(19) | N(4)—C(11)—C(10) | 116.4(2) |
| C(5)—C(9)—C(16) | 116.00(19) | N(4)—C(11)—C(15) | 123.6(2) |
| N(3)—C(10)—C(3) | 125.3(2) | C(15)—C(11)—C(10) | 119.9(2) |
| N(4)—C(12)—C(13) | 123.6(3) | C(18)—C(17)—C(16) | 115.8(2) |
| C(12)—C(13)—C(14) | 119.1(2) | O(1)—C(18)—C(17) | 109.3(2) |
| C(15)—C(14)—C(13) | 118.4(2) | O(2)—C(18)—O(1) | 124.2(2) |
| C(14)—C(15)—C(11) | 118.8(2) | O(2)—C(18)—C(17) | 126.6(2) |
| C(17)—C(16)—C(9) | 107.3(2) | C(21)—C(20)—C(4) | 120.0(2) |
| C(1)—C(21)—C(20) | 119.1(2) | O(3)—C(22)—C(23) | 113.0(2) |

TABLE 6

Bond torsion angle (°) data of the ethanolate
of the compound of Formula I wherein R is methyl

| Bond | Torsion angle (°) | Bond | Torsion angle (°) |
|---|---|---|---|
| Br(1)—C(1)—C(2)—C(3) | −174.59(17) | N(2)—C(5)—C(9)—N(3) | −102.1(3) |
| Br(1)—C(1)—C(21)—C(20) | 174.62(19) | N(2)—C(5)—C(9)—C(16) | 19.0(3) |
| N(1)—C(4)—C(20)—C(21) | −176.5(2) | N(2)—C(6)—C(7)—N(1) | −0.1(3) |
| N(1)—C(5)—C(9)—N(3) | 71.7(3) | N(2)—C(6)—C(7)—C(8) | −176.9(2) |
| N(1)—C(5)—C(9)—C(16) | −167.2(2) | N(3)—C(9)—C(16)—C(17) | −60.3(2) |
| N(3)—C(10)—C(11)—N(4) | −153.5(2) | C(1)—C(2)—C(3)—C(10) | 176.7(2) |
| N(3)—C(10)—C(11)—C(15) | 23.0(3) | C(2)—C(1)—C(21)—C(20) | −3.8(4) |
| N(4)—C(11)—C(15)—C(14) | −0.2(4) | C(2)—C(3)—C(4)—N(1) | 176.6(2) |
| N(4)—C(12)—C(13)—C(14) | −0.7(4) | C(2)—C(3)—C(4)—C(20) | −3.2(4) |
| C(1)—C(2)—C(3)—C(4) | −0.4(3) | C(2)—C(3)—C(10)—N(3) | −130.2(3) |
| C(2)—C(3)—C(10)—C(11) | 49.3(3) | C(4)—N(1)—C(5)—C(9) | 3.2(3) |
| C(3)—C(4)—C(20)—C(21) | 3.3(4) | C(4)—N(1)—C(7)—C(6) | −178.4(2) |
| C(3)—C(10)—C(11)—N(4) | 26.9(3) | C(4)—N(1)—C(7)—C(8) | −1.4(4) |
| C(3)—C(10)—C(11)—C(15) | −156.5(2) | C(4)—C(3)—C(10)—N(3) | 46.7(4) |
| C(4)—N(1)—C(5)—N(2) | 178.27(19) | C(4)—C(3)—C(10)—C(11) | −133.8(2) |
| C(4)—C(20)—C(21)—C(1) | 0.2(4) | C(5)—N(2)—C(6)—C(7) | −0.4(3) |
| C(5)—N(1)—C(4)—C(3) | −44.1(3) | C(5)—C(9)—C(16)—C(17) | −178.74(19) |
| C(5)—N(1)—C(4)—C(20) | 135.7(2) | C(6)—N(2)—C(5)—N(1) | 0.7(3) |
| C(5)—N(1)—C(7)—C(6) | 0.6(3) | C(6)—N(2)—C(5)—C(9) | 175.1(2) |
| C(5)—N(1)—C(7)—C(8) | 177.6(2) | C(7)—N(1)—C(4)—C(3) | 134.8(2) |
| C(7)—N(1)—C(4)—C(20) | −45.4(3) | C(9)—C(16)—C(17)—C(18) | −179.3(2) |
| C(7)—N(1)—C(5)—N(2) | −0.8(2) | C(10)—N(3)—C(9)—C(5) | −70.0(2) |
| C(7)—N(1)—C(5)—C(9) | −175.84(19) | C(10)—N(3)—C(9)—C(16) | 164.8(2) |
| C(9)—N(3)—C(10)—C(3) | −1.6(4) | C(10)—C(3)—C(4)—N(1) | −0.3(3) |
| C(9)—N(3)—C(10)—C(11) | 178.83(19) | C(10)—C(3)—C(4)—C(20) | 179.9(2) |
| C(10)—C(11)—C(15)—C(14) | −176.5(2) | C(13)—C(14)—C(15)—C(11) | 0.1(4) |
| C(11)—N(4)—C(12)—C(13) | 0.5(3) | C(16)—C(17)—C(18)—O(1) | −168.7(2) |
| C(12)—N(4)—C(11)—C(10) | 176.34(19) | C(16)—C(17)—C(18)—O(2) | 12.9(4) |
| C(12)—N(4)—C(11)—C(15) | −0.1(3) | C(19)—O(1)—C(18)—O(2) | 1.1(4) |
| C(12)—C(13)—C(14)—C(15) | 0.3(4) | C(19)—O(1)—C(18)—C(17) | −177.4(2) |
| C(21)—C(1)—C(2)—C(3) | 3.9(4) | | |

B: Preparation of the Hydrochloride of the Compound of Formula II-2 (the Compound of Formula I Wherein R is Ethyl)

B-1: Use of a Solution B that can Generate HCl as HCl Donor A

Example 7: Using Acetyl Chloride-Absolute Ethanol Solution

The compound of Formula II-2 (1.38 g, 3 mmol) was dissolved in absolute ethanol (5 ml) at 13° C., and then an absolute ethanol solution (5 ml) containing acetyl chloride (3 mmol) was added dropwise, and reacted overnight. Then, MTBE (45 ml) was added dropwise to the above reaction mixture, reacted for 0.5 h, and then filtered. The filter cake was dissolved in 30 ml absolute ethanol, decolorized at 50° C. for 0.5 h, and then filtered. The filtrate was concentrated, and the residue was dissolved with absolute ethanol (12 ml) at 50° C., and then MTBE (6 ml) was added dropwise to it. The solution became turbid and was stirred for 0.5 h. MTBE (82 ml) was added dropwise to the above mixture. Then, it was cooled to −8° C. and stirred for 1 h, and then filtered. The filter cake was subjected to pulping with ether (25 ml) for 1.5 h, and then filtered. The filter cake was dried to obtain 1.3 g of a white solid, with a yield of 92%, purity: 99.73%, m.p: 160-163° C. Theoretical value of chloride ion content was 7.24% (w/w), and the measured value was 7.31% (w/w). See FIG. 5 for the X-ray powder diffraction pattern of the crystal.

Example 8: Using Acetyl Chloride-Isopropanol Solution

With reference to the operation of Example 7, the target compound was prepared by crystallizing at 20° C., with the compound of Formula II-2 and acetyl chloride-anhydrous isopropanol solution as starting materials (with a molar ratio of 1:1). See FIG. 6 for the X-ray powder diffraction pattern of the crystal. Theoretical value of chloride ion content was 7.24% (w/w), and the measured value was 7.21% (w/w).

B-2: Use of a HCl-Anhydrous Alcohol Solution as HCl Donor A

Example 9: Using HCl-Anhydrous Ethanol Solution

The compound of Formula II-2 (1.38 g, 3 mmol) was dissolved in absolute ethanol (5 ml) at 13° C., and then 1.2 g absolute ethanol-HCl (HCl content of 8.87%) (with HCl molar quantity of 3 mmol) was added dropwise thereto, and reacted for 0.5 h. Then, MTBE (45 ml) was added dropwise to the above reaction mixture, reacted for 0.5 h, and then filtered. The filter cake was dissolved in 30 ml absolute ethanol, decolorized at 50° C. for 0.5 h, and then filtered. The filtrate was concentrated, and the residue was dissolved with absolute ethanol (12 ml) at 50° C., and then MTBE (60 ml) was added dropwise thereto. The solution became turbid and was stirred for 0.5 h. MTBE (82 ml) was then added dropwise. Then, it was cooled to −8° C. and stirred for 1 h, the mixture was filtered, and the filter cake was subjected to slurrying with ether (25 ml) for 1.5 h, and then filtered. The filter cake was dried to obtain 1.3 g of a white solid, with a yield of 92%, purity: 99.89%, m.p: 162-165° C. Theoretical value of chloride ion content was 7.24% (w/w), and the measured value was 7.15% (w/w). See FIG. 7 for the X-ray powder diffraction pattern of the crystal.

Figure 8:
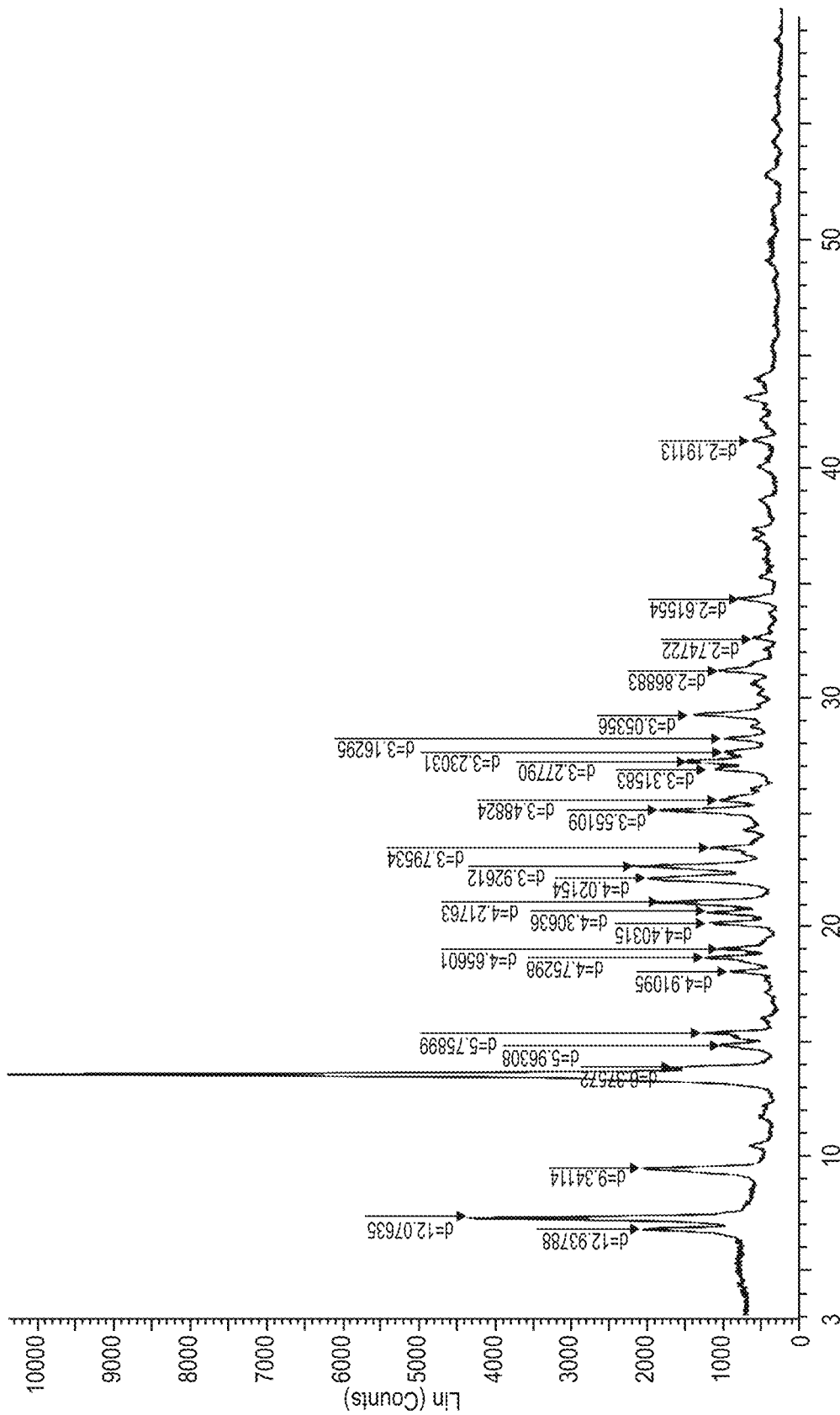
FIG. 8: An X-ray powder diffraction pattern of the crystal of a compound of Formula I wherein R=CH₂CH₃ (EL-001A2018010801)

With reference to the operation of Example 9, another batch of the crystal of the compound of Formula I wherein R is ethyl was obtained. The X-ray powder diffraction pattern of the crystal is shown in FIG. 8.

Example 10: Using HCl-Anhydrous Ethanol Solution

With reference to the operation of Example 9, the crystallization solvent ethanol: methyl tert-butyl ether=1:7 (v/v) was used, and the crystal of the compound of Formula I wherein R is ethyl was obtained. Theoretical value of chloride ion content was 7.24% (w/w), and the measured value was 7.19% (w/w). See FIG. 9 for the X-ray powder diffraction pattern of the crystal.

B-3: Use of Amino Acid Hydrochloride as HCl Donor A

Example 11: Using Glycine Hydrochloride

Glycine hydrochloride (2.46 g, 22 mmol) was added in absolute ethanol (50 ml) at 60° C., and then an absolute ethanol solution (15 ml) containing the compound of Formula II-2 (5 g, 11 mmol) was added dropwise within 5 minutes, and allowed to react for 0.5 h. The reaction mixture was cooled to −20° C. and maintained overnight, and then filtered. The filtrate was concentrated, and the residue was dissolved in absolute ethanol (50 ml), decolorized at 55-60° C. for 0.5 h, and filtered. The filtrate was concentrated. The residue was dissolved in absolute ethanol (20 ml) at 60° C. Butyl tert-butyl ether (140 ml) was added dropwise. Then, it was cooled to room temperature, stirred overnight, and filtered. The filter cake was dried to obtain the target product. Theoretical value of chloride ion content was 7.24% (w/w), and the measured value was 6.82% (w/w). See FIG. 10 for the X-ray powder diffraction pattern of the crystal.

Figure 11:
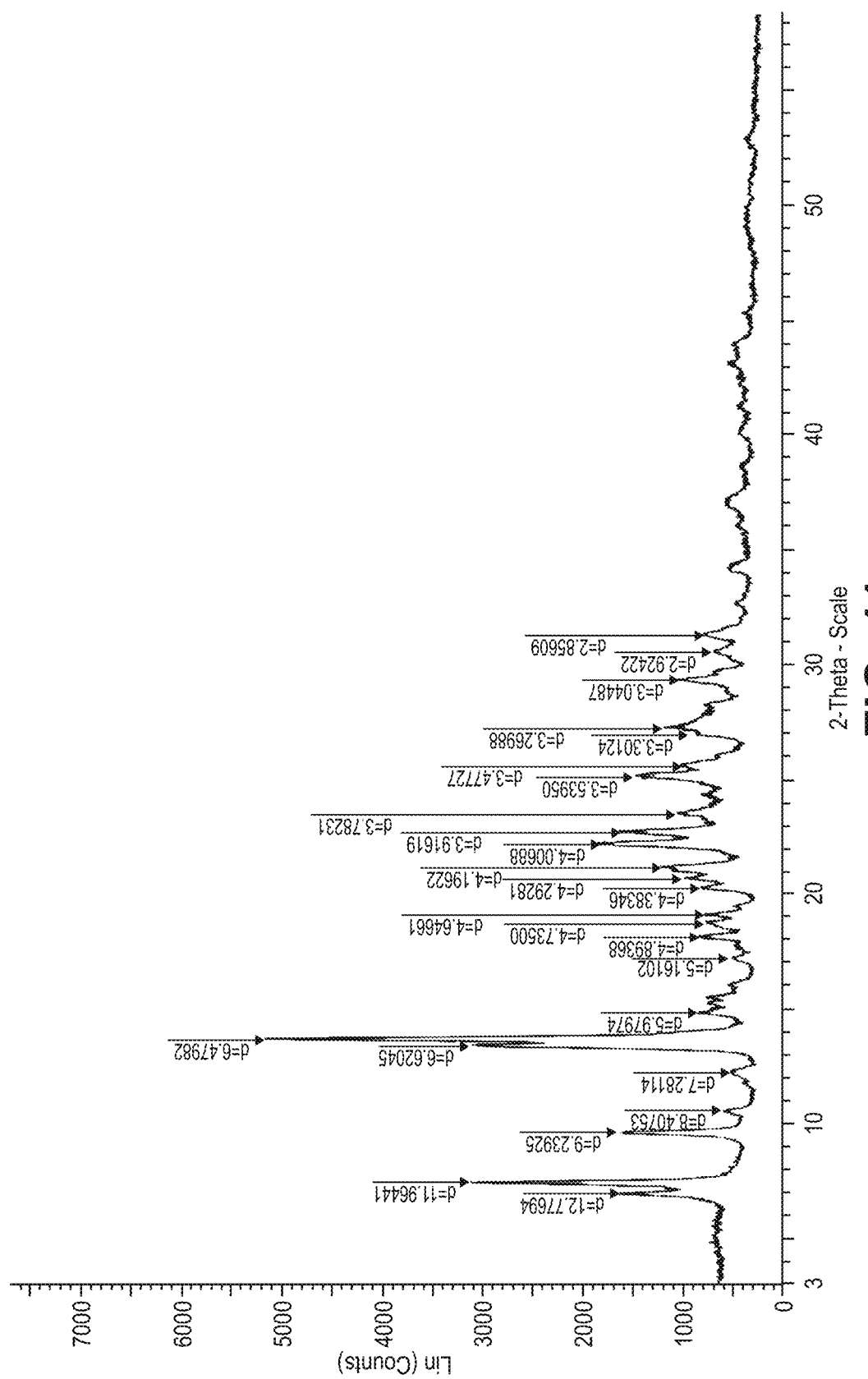
FIG. 11: An X-ray powder diffraction pattern of the crystal of a compound of Formula I wherein R=CH₂CH₃ (EL-001AG2017122101)

With reference to the operation of Example 11, another batch of the crystal of the compound of Formula I wherein R is ethyl was obtained. The X-ray powder diffraction pattern of the crystal is shown in FIG. 11.

Example 12: Using Glycine Hydrochloride

Glycine hydrochloride (2.46 g, 22 mmol) was added in absolute ethanol (50 ml) at 60° C., and then an absolute ethanol solution (15 ml) containing the compound of Formula II-2 (5 g, 11 mmol) was added dropwise within 5 minutes, and allowed to react for 0.5 h. It was cooled to −20° C. and maintained overnight, then filtered. The filtrate was concentrated, and the residue was dissolved in absolute ethanol (50 ml), decolorized at 55-60° C. for 0.5 h, and then filtered. The filtrate was concentrated, and the residue was dissolved with absolute ethanol (25 ml) at 60° C., and ethyl acetate (240 ml) was added dropwise thereto. Then, it was cooled to −40° C., stirred for 2 h, and filtered. The residue was dissolved in absolute ethanol (25 ml) at 50° C., and methyl tert-butyl ether (150 ml) was added dropwise thereto. Then, it was cooled to room temperature, stirred for 1 h, and filtered. The filter cake was dried to obtain the target product. Theoretical value of chloride ion content was 7.24% (w/w), and the measured value was 7.02% (w/w). See FIG. 12 for the X-ray powder diffraction pattern of the crystal.

Figure 13:
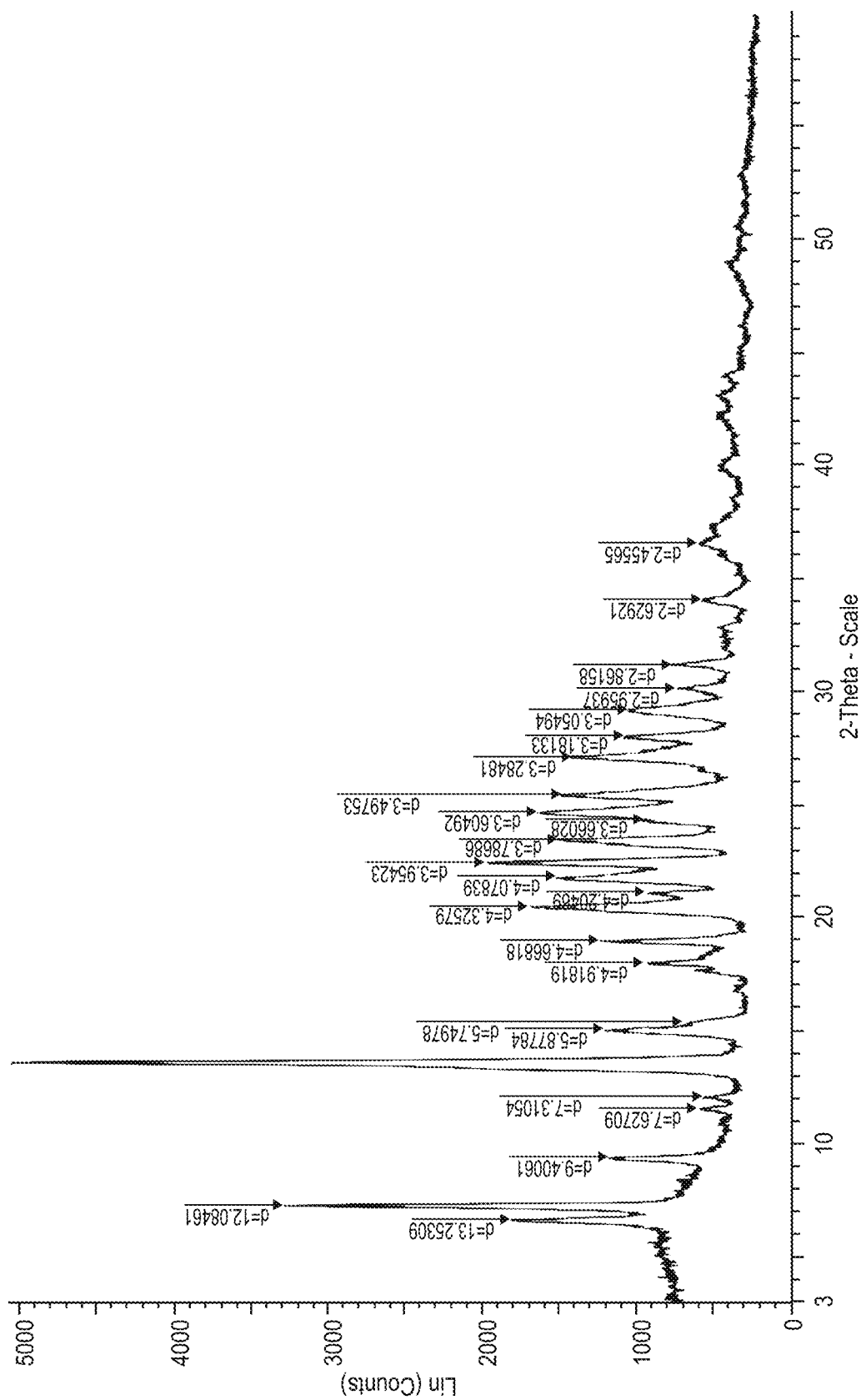
FIG. 13: An X-ray powder diffraction pattern of the crystal of a compound of Formula I wherein R=CH₂CH₃ (EL-001AG2018010201).

With reference to the operation of Example 12, another batch of the crystal of the compound of Formula I wherein R is ethyl was obtained. The X-ray powder diffraction pattern of the crystal is shown in FIG. 13.

Example 13: Preparation of the Compound of Formula I Wherein R is Ethyl Using Valine Hydrochloride With reference to the operation of Example 11, the target product was obtained by crystallizing at −10° C. with the compound of Formula II-2 and valine hydrochloride as starting materials (with a molar ratio of 1:1.5), and ethanol and isopropyl ether as the crystallization solvent. Theoretical value of chloride ion content was 7.24% (w/w), and the measured value was 6.74% (w/w).

Example 14: Preparation of the Compound of Formula I Wherein R is Ethyl

With reference to the operation of Example 11, the target compound was prepared with the compound of Formula II-2 and alanine hydrochloride as starting materials (with a molar ratio of 1:3). Theoretical value of chloride ion content was 7.24% (w/w), and the measured value was 6.63% (w/w).

Example 15: Preparation and Structural Characterization of the Compound of Formula I Wherein R is Ethyl The II-2 hydrochloride prepared in Example 9 was recrystallized with ethanol and methyl tert-butyl ether, and allowed to stand at room temperature for 4 days. The crystals were collected and subjected to an X-ray single crystal diffraction experiment. The crystal parameters are shown in Tables 7-12 below.

TABLE 7

Crystal data and structure refinement data of the ethanolate of the compound of Formula 1 wherein R is ethyl

| Bond precision: | C—C = 0.0051 A | Wavelength = 1.54184 | |
|---|---|---|---|
| Cell: | a = 7.3774 (1) | b = 12.7332 (2) | c = 27.1779 (4) |
| | alpha = 90 | beta = 90 | gamma = 90 |
| Temperature: | 150 K | | |

| | Calculated | Reported |
|---|---|---|
| Volume | 2553.04 (6) | 2553.04 (6) |
| Space group | P 21 21 21 | P 21 21 21 |
| Hall group | P 2ac 2ab | P 2ac 2ab |
| Moiety formula | C22 H22 Br N4 O2, C2 H6 O, Cl | C22 H22 Br N4 O2, C2 H6 O, Cl |
| Sum formula | C24 H28 Br Cl N4 O3 | C24 H28 Br Cl N4 O3 |
| Mr | 535.85 | 535.85 |
| Dx, b cm-3 | 1.394 | 1.394 |
| Z | 4 | 4 |
| Mu (mm-1) | 3.419 | 3.419 |
| F000 | 1104.0 | 1104.0 |
| F000' | 1105.42 | |
| H, k, lmax | 9, 15, 33 | 8, 15, 33 |
| Nref | 5191 [2973] | 4625 |
| Tmin, Tmax | | 0.276, 1.000 |
| Tmin' | | |

Correction method = # Reported T Limits: Tmin = 0.276 Tmax = 1.000
AbsCorr = MULTI-SCAN
Data Completeness = 1.56/0.89      Theta(max) = 74.052
R(reflections) = 0.0303 (4503)      wR2 (reflections) = 0.0795 (4625)
S = 1.035      Npar = 302

TABLE 8

Data of non-hydrogen atom coordinates (×10⁴) and equivalent isotropic shift parameter (Å2 × 10³) of the ethanate of the compound of Formula I wherein R is ethyl

| No. of Atom | x | y | z | U(eq) |
|---|---|---|---|---|
| Br(1) | −3552(1) | 10601(1) | 5747(1) | 37(1) |
| O(1) | 4576(6) | 4196(2) | 6487(2) | 73(1) |
| N(1) | 3579(4) | 9375(2) | 6716(1) | 24(1) |
| N(2) | 5735(4) | 8340(2) | 6948(1) | 28(1) |
| O(3) | 2760(4) | 4013(2) | 5838(1) | 46(1) |
| N(4) | 2822(4) | 9849(2) | 5048(1) | 31(1) |
| N(3) | 3572(4) | 7810(2) | 5886(1) | 24(1) |
| C(11) | 2919(4) | 8840(3) | 5178(1) | 23(1) |
| C(7) | 4778(5) | 9987(3) | 6995(1) | 28(1) |
| C(2) | −125(4) | 9623(2) | 5794(1) | 24(1) |
| C(22) | −855(5) | 10674(3) | 6501(1) | 29(1) |
| C(16) | 3957(5) | 6435(3) | 6506(1) | 28(1) |
| C(3) | 1528(4) | 9324(2) | 6006(1) | 24(1) |
| C(6) | 6102(5) | 9324(3) | 7136(1) | 31(1) |
| C(4) | 1938(4) | 9694(3) | 6478(1) | 23(1) |
| C(1) | −1287(5) | 10272(2) | 6046(1) | 27(1) |
| C(5) | 4197(5) | 8375(3) | 6699(1) | 25(1) |
| C(10) | 2729(4) | 8615(2) | 5715(1) | 24(1) |
| C(21) | 759(5) | 10376(3) | 6721(1) | 27(1) |
| C(8) | 4561(5) | 11133(3) | 7077(1) | 34(1) |
| C(15) | 3156(5) | 8029(3) | 4848(1) | 33(1) |
| C(14) | 3266(6) | 8272(3) | 4351(1) | 39(1) |
| C(9) | 3279(4) | 7547(2) | 6409(1) | 24(1) |
| C(12) | 2931(5) | 10065(3) | 4565(1) | 34(1) |
| C(18) | 3569(6) | 4567(3) | 6194(1) | 38(1) |
| C(13) | 3142(5) | 9305(3) | 4208(1) | 34(1) |
| C(17) | 2968(5) | 5690(3) | 6167(1) | 36(1) |
| C(19) | 3152(8) | 2898(3) | 5820(2) | 60(1) |
| C(20) | 1904(10) | 2421(3) | 5460(2) | 74(2) |
| O(2) | 12010(4) | 7592(3) | 7610(1) | 50(1) |
| C(23) | 11583(7) | 8592(3) | 7804(2) | 48(1) |
| C(24) | 10366(10) | 8548(4) | 8231(2) | 83(2) |
| Cl(1) | 8848(1) | 6748(1) | 6988(1) | 34(1) |

Note:
U(eq) is defined as one third of the trace of the orthogonalized $U^{ij}$ tensor.

TABLE 9

Data of non-hydrogen atom isotropic shift parameter (Å2 × 10³) of the ethanate of the compound of Formula I wherein R is ethyl

| No. of Atom | U¹¹ | U²² | U³³ | U²³ | U¹³ | U¹² |
|---|---|---|---|---|---|---|
| Br(1) | 30(1) | 42(1) | 39(1) | 4(1) | −2(1) | 9(1) |
| O(1) | 88(3) | 35(2) | 96(3) | 4(2) | −51(2) | 17(2) |
| N(1) | 25(1) | 27(1) | 21(1) | −2(1) | −1(1) | −6(1) |
| N(2) | 25(1) | 33(2) | 27(1) | 4(1) | −2(1) | 0(1) |
| O(3) | 68(2) | 21(1) | 49(2) | −3(1) | −9(2) | 12(1) |
| N(4) | 42(2) | 25(1) | 25(1) | 1(1) | 2(1) | −1(1) |
| N(3) | 28(1) | 23(1) | 22(1) | −1(1) | 1(1) | 2(1) |
| C(11) | 21(2) | 25(2) | 23(1) | −2(1) | 0(1) | 1(1) |
| C(7) | 29(2) | 36(2) | 21(1) | −5(1) | 2(1) | −8(2) |
| C(2) | 26(2) | 20(1) | 26(1) | 1(1) | 1(1) | −3(1) |
| C(22) | 31(2) | 23(2) | 34(2) | −3(1) | 9(1) | 0(1) |
| C(16) | 26(2) | 29(2) | 30(2) | 2(1) | −3(1) | 1(1) |
| C(3) | 26(2) | 21(1) | 25(1) | −2(1) | 2(1) | −2(1) |
| C(6) | 27(2) | 39(2) | 27(1) | −3(1) | −4(1) | −6(2) |
| C(4) | 22(2) | 24(2) | 23(1) | −2(1) | 1(1) | −2(1) |
| C(1) | 24(2) | 24(1) | 34(2) | 4(1) | 4(1) | −4(1) |
| C(5) | 27(2) | 28(2) | 21(1) | 0(1) | 2(1) | −1(1) |
| C(10) | 26(2) | 22(1) | 24(1) | −3(1) | 1(1) | −2(1) |
| C(21) | 28(2) | 27(2) | 25(1) | −5(1) | 3(1) | −3(1) |
| C(8) | 32(2) | 36(2) | 34(2) | −13(2) | 2(1) | −8(2) |
| C(15) | 46(2) | 27(2) | 27(2) | −4(1) | 3(2) | 8(2) |
| C(14) | 50(2) | 40(2) | 26(2) | −9(1) | 1(2) | 8(2) |
| C(9) | 24(2) | 25(2) | 24(1) | 2(1) | 2(1) | 2(1) |
| C(12) | 44(2) | 31(2) | 27(2) | 6(1) | 0(2) | −1(2) |
| C(18) | 43(2) | 25(2) | 46(2) | 3(2) | −6(2) | 5(2) |
| C(13) | 33(2) | 45(2) | 24(1) | 2(1) | 0(1) | −2(2) |
| C(17) | 42(2) | 22(2) | 45(2) | 2(2) | −13(2) | 3(2) |
| C(19) | 85(4) | 21(2) | 73(3) | −7(2) | −4(3) | 17(2) |
| C(20) | 127(5) | 24(2) | 72(3) | −10(2) | −6(4) | 4(3) |
| O(2) | 37(2) | 65(2) | 47(2) | −18(1) | −12(1) | 14(1) |
| C(23) | 49(2) | 43(2) | 50(2) | 4(2) | 2(2) | −7(2) |
| C(24) | 116(5) | 50(3) | 81(3) | −28(3) | 49(4) | −19(2) |
| Cl(1) | 28(1) | 42(1) | 30(1) | −4(1) | 0(1) | 0(1) |

TABLE 10

Data of hydrogen atom coordinates (×10⁴) and equivalent isotropic shift parameter (Å2 × 10³) of the ethanate of the compound of Formula I wherein R is ethyl

| No. of hydrogen atom | x | y | z | U(eq) |
|---|---|---|---|---|
| H(2) | 6416 | 7778 | 6987 | 34 |
| H(2A) | −443 | 9376 | 5476 | 29 |
| H(22) | −1652 | 11149 | 6662 | 35 |
| H(16A) | 5278 | 6396 | 6444 | 34 |
| H(16B) | 3731 | 6240 | 6853 | 34 |
| H(6) | 7121 | 9503 | 7333 | 37 |
| H(21) | 1064 | 10636 | 7038 | 32 |
| H(8A) | 4204 | 11472 | 6768 | 51 |
| H(8B) | 5713 | 11430 | 7191 | 51 |
| H(8C) | 3623 | 11253 | 7326 | 51 |
| H(15) | 3242 | 7322 | 4958 | 40 |
| H(14) | 3424 | 7733 | 4113 | 47 |
| H(9) | 1950 | 7574 | 6480 | 29 |
| H(12) | 2860 | 10778 | 4464 | 41 |
| H(13) | 3200 | 9492 | 3870 | 41 |
| H(17A) | 1658 | 5721 | 6245 | 44 |
| H(17B) | 3123 | 5938 | 5825 | 44 |
| H(19A) | 2972 | 2579 | 6148 | 71 |
| H(19B) | 4425 | 2782 | 5718 | 71 |
| H(20A) | 2128 | 2722 | 5134 | 112 |
| H(20B) | 649 | 2563 | 5558 | 112 |
| H(20C) | 2105 | 1660 | 5449 | 112 |
| H(2B) | 11129 | 7368 | 7445 | 74 |
| H(23A) | 11005 | 9020 | 7544 | 57 |
| H(23B) | 12720 | 8948 | 7902 | 57 |
| H(24A) | 9274 | 8150 | 8145 | 124 |
| H(24B) | 10026 | 9262 | 8328 | 124 |
| H(24C) | 10986 | 8201 | 8506 | 124 |

TABLE 11

Data of bond length (Å) and bond angle (°) of the ethanolate of the compound of Formula I in which R is ethyl

| Bond | Bond length Å (bond angle°) | Bond | Bond length Å (bond angle°) |
|---|---|---|---|
| Br(1)—C(1) | 1.904(4) | O(1)—C(18) | 1.186(5) |
| N(1)—C(7) | 1.402(4) | N(1)—C(4) | 1.431(5) |
| N(1)—C(5) | 1.354(4) | N(2)—C(6) | 1.380(4) |
| N(2)—C(5) | 1.321(4) | O(3)—C(18) | 1.340(5) |
| O(3)—C(19) | 1.450(4) | N(4)—C(11) | 1.334(4) |
| N(4)—C(12) | 1.345(4) | N(3)—C(10) | 1.286(4) |
| N(3)—C(9) | 1.478(4) | C(11)—C(10) | 1.493(4) |
| C(11)—C(15) | 1.380(5) | C(7)—C(6) | 1.347(5) |
| C(7)—C(8) | 1.485(5) | C(2)—C(3) | 1.401(4) |
| C(2)—C(1) | 1.373(5) | C(22)—C(1) | 1.376(5) |
| C(22)—C(21) | 1.386(5) | C(16)—C(9) | 1.523(4) |
| C(16)—C(17) | 1.509(5) | C(3)—C(4) | 1.401(4) |
| C(3)—C(10) | 1.491(4) | C(4)—C(21) | 1.395(4) |
| C(5)—C(9) | 1.481(4) | C(15)—C(14) | 1.390(5) |

TABLE 11-continued

Data of bond length (Å) and bond angle (°) of the ethanolate of the compound of Formula I in which R is ethyl

| Bond | Bond length Å (bond angle°) | Bond | Bond length Å (bond angle°) |
|---|---|---|---|
| C(14)—C(13) | 1.374(5) | C(12)—C(13) | 1.379(5) |
| C(18)—C(17) | 1.498(5) | C(19)—C(20) | 1.474(7) |
| O(2)—C(23) | 1.415(5) | C(23)—C(24) | 1.468(7) |
| C(7)—N(1)—C(4) | 128.3(3) | C(18)—O(3)—C(19) | 116.8(3) |
| C(5)—N(1)—C(7) | 109.2(3) | C(11)—N(4)—C(12) | 116.9(3) |
| C(5)—N(1)—C(4) | 122.5(3) | C(10)—N(3)—C(9) | 117.2(3) |
| C(5)—N(2)—C(6) | 109.1(3) | N(4)—C(11)—C(10) | 116.1(3) |
| N(4)—C(11)—C(15) | 123.7(3) | C(6)—C(7)—C(8) | 130.7(3) |
| C(15)—C(11)—C(10) | 120.2(3) | C(1)—C(2)—C(3) | 120.2(3) |
| N(1)—C(7)—C(8) | 124.0(3) | C(1)—C(22)—C(21) | 119.0(3) |
| C(6)—C(7)—N(1) | 105.2(3) | C(17)—C(16)—C(9) | 108.7(3) |
| C(2)—C(3)—C(4) | 118.2(3) | C(3)—C(4)—N(1) | 120.1(3) |
| C(2)—C(3)—C(10) | 117.7(3) | C(21)—C(4)—N(1) | 119.4(3) |
| C(4)—C(3)—C(10) | 124.1(3) | C(21)—C(4)—C(3) | 120.5(3) |
| C(7)—C(6)—N(2) | 108.8(3) | C(2)—C(1)—Br(1) | 117.9(2) |
| C(2)—C(1)—C(22) | 121.8(3) | N(2)—C(5)—C(9) | 129.9(3) |
| C(22)—C(1)—Br(1) | 120.3(3) | N(3)—C(10)—C(11) | 117.4(3) |
| N(1)—C(5)—C(9) | 122.2(3) | N(3)—C(10)—C(3) | 125.4(3) |
| N(2)—C(5)—N(1) | 107.7(3) | C(3)—C(10)—C(11) | 117.2(3) |
| C(22)—C(21)—C(4) | 120.2(3) | C(22)—C(21)—C(4) | 120.2(3) |
| C(11)—C(15)—C(14) | 118.2(3) | C(11)—C(15)—C(14) | 118.2(3) |
| C(13)—C(14)—C(15) | 119.0(3) | C(13)—C(14)—C(15) | 119.0(3) |
| N(3)—C(9)—C(16) | 109.1(2) | N(3)—C(9)—C(16) | 109.1(2) |
| C(22)—C(21)—C(4) | 120.2(3) | N(3)—C(9)—C(5) | 106.5(3) |
| C(11)—C(15)—C(14) | 118.2(3) | C(5)—C(9)—C(16) | 114.8(3) |
| C(13)—C(14)—C(15) | 119.0(3) | N(4)—vC(12)—C(13) | 123.4(3) |
| N(3)—C(9)—C(16) | 109.1(2) | O(1)—C(18)—O(3) | 123.6(3) |
| O(1)—C(18)—C(17) | 126.8(4) | C(18)—C(17)—C(16) | 115.3(3) |
| O(3)—C(18)—C(17) | 109.6(3) | O(3)—C(19)—C(20) | 107.5(4) |
| C(14)—C(13)—C(12) | 118.7(3) | O(2)—C(23)—C(24) | 113.4(4) |

TABLE 12

Data of bond torsion angle (°) of the ethanolate of the compound of Formula I wherein R is ethyl

| Bond | Torsion angle (°) | Bond | Torsion angle (°) |
|---|---|---|---|
| O(1)—C(18)—C(17)—C(16) | 8.9(7) | N(1)—C(5)—C(9)—C(16) | −169.6(3) |
| N(1)—C(7)—C(6)—N(2) | 0.3(4) | N(2)—C(5)—C(9)—N(3) | −105.1(4) |
| N(1)—C(4)—C(21)—C(22) | −178.5(3) | N(2)—C(5)—C(9)—C(16) | 15.8(5) |
| N(1)—C(5)—C(9)—N(3) | 69.5(4) | O(3)—C(18)—C(17)—C(16) | −172.3(3) |
| N(4)—C(11)—C(10)—N(3) | −149.5(3) | C(11)—N(4)—C(12)—C(13) | −0.3(6) |
| N(4)—C(11)—C(10)—C(3) | 32.4(4) | C(11)—C(15)—C(14)—C(13) | 0.3(6) |
| N(4)—C(11)—C(15)—C(14) | −1.3(6) | C(7)—N(1)—C(4)—C(3) | 138.6(3) |
| N(4)—C(12)—C(13)—C(14) | −0.7(6) | C(7)—N(1)—C(4)—C(21) | −41.4(4) |
| C(7)—N(1)—C(5)—N(2) | −1.0(3) | C(2)—C(3)—C(10)—N(3) | −135.7(3) |
| C(7)—N(1)—C(5)—C(9) | −176.7(3) | C(2)—C(3)—C(10)—C(11) | 42.2(4) |
| C(2)—C(3)—C(4)—N(1) | 177.6(3) | C(3)—C(2)—C(1)—Br(1) | −177.5(2) |
| C(2)—C(3)—C(4)—C(21) | −2.5(4) | C(3)—C(2)—C(1)—C(22) | 2.1(5) |
| C(3)—C(4)—C(21)—C(22) | 1.6(5) | C(4)—N(1)—C(7)—C(8) | −2.6(5) |
| C(6)—N(2)—C(5)—N(1) | 1.2(3) | C(4)—N(1)—C(5)—N(2) | 179.4(2) |
| C(6)—N(2)—C(5)—C(9) | 176.4(3) | C(4)—N(1)—C(5)—C(9) | 3.7(4) |
| C(4)—N(1)—C(7)—C(6) | −180.0(3) | C(4)—C(3)—C(10)—N(3) | 43.3(5) |
| C(4)—C(3)—C(10)—C(11) | −138.8(3) | C(5)—N(1)—C(7)—C(6) | 0.4(3) |
| C(1)—C(2)—C(3)—C(4) | 0.7(4) | C(5)—N(1)—C(7)—C(8) | 177.8(3) |
| C(1)—C(2)—C(3)—C(10) | 179.8(3) | C(5)—N(1)—C(4)—C(3) | −41.9(4) |
| C(1)—C(22)—C(21)—C(4) | 1.2(5) | C(5)—N(1)—C(4)—C(21) | 138.2(3) |
| C(5)—N(2)—C(6)—C(7) | −0.9(4) | C(10)—C(3)—C(4)—N(1) | −1.4(5) |
| C(10)—N(3)—C(9)—C(16) | 165.0(3) | C(10)—C(3)—C(4)—C(21) | 178.5(3) |
| C(10)—N(3)—C(9)—C(5) | −70.5(4) | C(21)—C(22)—C(1)—Br(1) | 176.5(2) |
| C(10)—C(11)—C(15)—C(14) | 177.9(3) | C(21)—C(22)—C(1)—C(2) | −3.1(5) |
| C(8)—C(7)—C(6)—N(2) | −176.9(3) | C(9)—N(3)—C(10)—C(1) | −175.9(3) |
| C(15)—C(11)—C(10)—N(3) | 31.3(5) | C(9)—N(3)—C(10)—C(3) | 2.0(5) |
| C(15)—C(11)—C(10)—C(3) | −146.8(3) | C(9)—C(16)—C(17)—C(18) | 176.3(3) |
| C(15)—C(14)—C(13)—C(12) | 0.6(6) | C(12)—N(4)—C(11)—C(10) | −177.9(3) |
| C(12)—N(4)—C(11)—C(15) | 1.3(6) | C(17)—C(16)—C(9)—C(5) | −177.2(3) |
| C(18)—O(3)—C(19)—C(20) | 170.6(4) | C(19)—O(3)—C(18)—O(1) | 0.6(7) |
| C(17)—C(16)—C(9)—N(3) | −57.7(4) | C(19)—O(3)—C(18)—C(17) | −178.2(4) |

Example 16: Stability Test of the Hydrochloride of the Benzodiazepine Derivative The compound of Formula I prepared in the above examples were selected, and placed under the conditions of 40° C., RH75% and 25° C., RH60% for an accelerated stability test and a long-term stability test after packaging. The changes in the degradation product (CNS-7054) in these compounds in 6 months were observed, and the results are shown in Table 13 below.

TABLE 13

Data of stability test of the hydrochloride of the benzodiazepine derivative

| R | Amino acid content | Change in CNS-7054 Accelerated experiment (40° C., RH75%) | Long-term experiment (25° C., RH60%) |
|---|---|---|---|
| Methyl | None | Not increased | Not increased |
| Methyl | 2% glycine | Not increased | Not increased |
| Methyl | 3% glycine | Not increased | Not increased |
| Methyl | 4% glycine | Increased by | Not increased |
| Methyl | 5% alanine | Increased by 0.01% | Not increased |
| Methyl | 4% valine | Increased by 0.01% | Not increased |
| Ethyl | None | Not increased | Not increased |
| Ethyl | 1.7% glycine | Not increased | Not increased |
| Ethyl | 2.8% glycine | Not increased | Not increased |
| Ethyl | 4.5% glycine | Not increased | Not increased |
| Ethyl | 4% alanine | Increased by 0.01% | Not increased |
| Ethyl | 5% alanine | Increased by 0.01% | Not increased |
| Ethyl | 4% valine | Increased by 0.01% | Not increased |

In addition, a lyophilized preparation made of sulfonates according to the prior art were partially degraded into carboxylic acid (CNS-7054) and released alcohol in both the accelerated and long-term experiments. The changes are shown in Table 14 below.

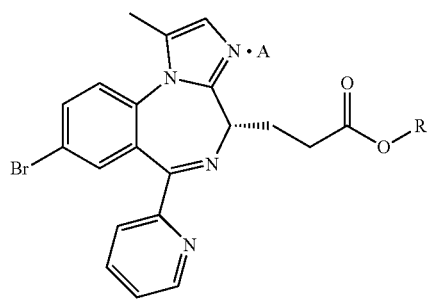

Sulfonate of benzazepine derivative

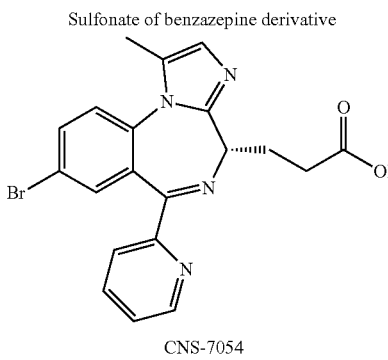

CNS-7054 wherein R is methyl or ethyl; A is benzenesulfonic acid or p-toluenesulfonic acid.

TABLE 14

Data of stability experiments of the sulfonate of the benzodiazepine derivative

| R | A | Class | CNS-7054 Accelerated experiment (40° C., RH75%) | Long-term experiment (25° C., RH60%) |
|---|---|---|---|---|
| Methyl | Benzenesulfonic acid | Drug substance | Increased by 0.07% in 1 month | Increased by 0.04% in 3 months |
| Methyl | Benzenesulfonic acid | Lyophilized preparation | Increased by 0.37% in 1 month | Increased by 0.35% in 3 months |
| Methyl | P-toluenesulfonic acid | Drug substance | Increased by 0.1% in 1 month | Increased by 0.1% in 3 months |
| Methyl | P-toluenesulfonic acid | Lyophilized preparation | Increased by 0.25% in 1 month | Increased by 0.2% in 3 months |
| Ethyl | Benzenesulfonic acid | Drug substance | Increased by 0.05% in 1 month | Increased by 0.03% in 3 months |
| Ethyl | Benzenesulfonic acid | Lyophilized preparation | Increased by 0.3% in 1 month | Increased by 0.26% in 3 months |
| Ethyl | P-toluenesulfonic acid | Drug substance | Increased by 0.2% in 1 month | Increased by 0.1% in 3 months |
| Ethyl | P-toluenesulfonic acid | Lyophilized preparation | Increased by 0.25% in 1 month | Increased by 0.15% in 3 months |

From the above data, it can be seen that the hydrochloride of the benzodiazepine derivative provided by the present invention has good stability, does not generate degradation products (CNS-7054), and does not generate genotoxic impurities.

Example 17: Determination of $ED_{50}$ and $LD_{50}$ in KM Mice for the Hydrochloride of the Benzodiazepine Derivative Sequential method was used to determine the hypnotic $ED_{50}$ and $LD_{50}$ in KM mice for the hydrochloride of the benzodiazepine derivative. Healthy and qualified male KM mice were selected, n=10–20. The drug was injected through the tail vein at a constant rate in 5 seconds. After preliminary pre-test, the approximate dosage that may cause hypnosis (or death) of the animals was found as an intermediate dosage in the formal experiment. A group interval of 0.8 was used, and 2-3 dosage groups were set up and down respectively. The formal experiment started with the administration from the intermediate dosage. When the animal was narcotized (or died), the dosage was reduced by one dose. If the animal was not narcotized (or died), the dosage was increased by one until 3-4 repetitions occurred. The $ED_{50}$ value and $LD_{50}$ value were measured with the disappearance of righting reflex or death as indicators. The therapeutic index (TI index=$ED_{50}/LD_{50}$) was calculated through $LD_{50}$ and $ED_{50}$ values. The experimental results are shown in Table 15 below.

TABLE 15

$ED_{50}$ and $LD_{50}$ data in KM mice for the hydrochloride of the benzodiazepine derivative

| No. | R | Acid | Amino acid content | $ED_{50}$(mg/kg, 95% confidence interval) | $LD_{50}$(mg/kg, 95% confidence interval) | TI |
|---|---|---|---|---|---|---|
| 1 | methyl | HCl | None | 35.20 (32.41~38.39) | 217.48 (192.55~245.23) | 6.2 |
| 2 | methyl | HCl | 3% glycine | 36.26 (33.57~40.11) | 224.82 (198.12~252.72) | 6.2 |
| 3 | ethyl | HCl | None | 13.21 (10.68~16.32) | 205.78 (187.43~226.14) | 15.6 |
| 4 | ethyl | HCl | 2.8% glycine | 13.53 (11.11~16.95) | 211.73 (193.08~232.18) | 15.6 |
| positive control 1 | Methyl | Benzene sulfonic acid | None | 40.64 (37.21~44.40) | 270.09 (237.72~306.88) | 6.6 |
| positive control 2 | Ethyl | Benzene sulfonic acid | None | 15.62 (13.14~18.56) | 263.14 (223.77~309.44) | 16.8 |

From the above data, it can be seen that the therapeutic index of the hydrochloride of the benzodiazepine derivative provided by the present invention is not significantly different from that of benzenesulfonate, and with good safety.

Example 18: 2*$ED_{50}$ Anesthesia Pharmacodynamics Experiment in KM Mice (n=20) for the Hydrochloride and Sulfonate of the Benzodiazepine Derivative KM mice, half male and half female, 20 mice in each group. With a dosage of 2*$ED_{50}$, it was injected into the tail vein at a constant rate in 5 seconds. The time of loss of the righting reflex in mice (induction time), recovery time (duration) and walking time were recorded. The experimental results are shown in Table 16 below.

TABLE 16

Experimental data of 2*$ED_{50}$ anesthesia pharmacodynamics in KM mice for the hydrochloride and sulfonate of the benzodiazepine derivative

| No. | R | Acid | A* | Dosage (2*ED50) | B* | C* | D* | E* | F* |
|---|---|---|---|---|---|---|---|---|---|
| 1 | Methyl | HCl | None | 70.40 mg/kg | 17.8 ± 2.06 | 674.3 ± 354.28 | 5/20 | 508.95 ± 510.89 | 8/20 |
| 2 | Methyl | HCl | 33% glycine | 72.52 mg/kg | 17.7 ± 2.12 | 673.3 ± 348.53 | 5/20 | 510.41 ± 512.25 | 8/20 |
| 3 | Ethyl | HCl | None | 26.42 mg/kg | 17.28 ± 2.04 | 462.75 ± 179.82 | 4/20 | 66.53 ± 149.76 | 3/20 |
| 4 | Ethyl | HCl | 2.8% glycine | 27.06 mg/kg | 17.35 ± 2.13 | 459.75 ± 184.15 | 4/20 | 67.75 ± 155.35 | 3/20 |
| Positive control 1 | Methyl | BSA* | None | 81.28 mg/kg | 17.6 ± 1.93 | 692.3 ± 399.15 | 9/20 | 514.95 ± 525.16 | 17/20 |

TABLE 16-continued

Experimental data of 2*ED$_{50}$ anesthesia pharmacodynamics in KM mice for the hydrochloride and sulfonate of the benzodiazepine derivative

| No. | R | Acid | A* | Dosage (2*ED50) | B* | C* | D* | E* | F* |
|---|---|---|---|---|---|---|---|---|---|
| Positive control 2 | Ethyl | BSA* | None | 31.24 mg/kg | 17.1 ± 2.00 | 443.75 ± 247.86 | 7/20 | 192.9 ± 268.98 | 10/20 |

Note:
A* = amino acid content;
B* = induction time (s);
C* = duration time (s);
D* = Number of animals with duration time longer than 10 min;
E* = Walking time (s);
F* = Number of animals with walking time longer than 1 min; and
BSA* = Benzenesulfonic acid From the above data, it can be seen that:

1. The benzodiazepine derivative wherein R is ethyl are better than that wherein R is methyl with respect to the duration time of anesthesia and walking time, with statistical differences.

2. With respect to the benzodiazepine derivative wherein R is ethyl, the incidence of the animal anesthesia time of more than 10 minutes is 35% for the sulfonate, and 20% for the hydrochloride. The incidence of the animal walking time of more than 1 min is 50% for the sulfonate and 15% for the hydrochloride, which indicates that the pharmacokinetic properties of the hydrochloride are more stable than those of the sulfonate, and are less affected by individual differences.

3. With respect to the benzodiazepine derivative wherein R is methyl, the incidence of the animal anesthesia time of more than 10 minutes is 45% for the sulfonate, and 25% for the hydrochloride. The incidence of the animal walking time of more than 1 min is 85% for the sulfonate and 40% for the hydrochloride, which indicates that the pharmacokinetic properties of the hydrochloride are more stable than those of the sulfonate, and are less affected by individual differences.

Conclusion: The hydrochloride of the benzodiazepine derivative provided by the present invention has more stable pharmacokinetic properties than sulfonates, and is less affected by individual differences.

What is claimed is:

1. A crystal form of ethyl (S)-3-(8-bromo-1-methyl-6-(pyridin-2-yl)-4H-benzo[f]imidazo[1,2-α][1,4]diazepin-4-yl)propanoate hydrochloride of Formula I:

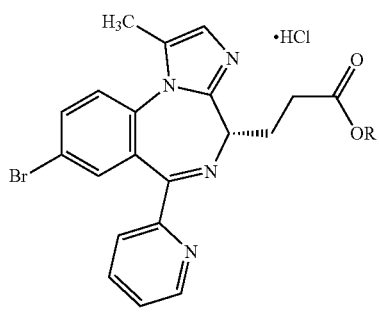

Formula I wherein R is CH$_2$CH$_3$;
wherein the crystal form is Form 1, Form 2, Form 3, or Form 4;
wherein Form 1 is characterized by an X-ray powder diffraction pattern comprising characteristic peaks at angles (° 2θ) of 7.39°±0.2 °2θ and 13.70°±0.2 °2θ;
wherein Form 2 is characterized by an X-ray powder diffraction pattern comprising characteristic peaks at angles (° 2θ) of 7.45°±0.2 °2θ and 13.71°±0.2 °2θ;
wherein Form 3 is characterized by an X-ray powder diffraction pattern comprising characteristic peaks at angles (° 2θ) of 7.37°±0.2 °2θ and 13.63°±0.2 °2θ;
wherein Form 4 is characterized by an X-ray powder diffraction pattern comprising characteristic peaks at angles (° 2θ) of 7.31°±0.2 °2θ and 13.56°±0.2 °2θ; and
wherein each X-ray powder diffraction pattern is measured on a diffractometer using CuKα radiation.

2. The crystal form according to claim 1, wherein the crystal form is Form 1, Form 2, Form 3, or Form 4;
wherein Form 1 is further characterized by an X-ray powder diffraction pattern comprising characteristic peaks at angles (°2θ) of 6.83°±0.2 °2θ and 22.66°±0.2 °2θ;
wherein Form 2 is further characterized by an X-ray powder diffraction pattern comprising characteristic peaks at angles (°2θ) of 6.96°±0.2 °2θ and 22.21°±0.2 °2θ;
wherein Form 3 is further characterized by an X-ray powder diffraction pattern comprising characteristic peaks at angles (°2θ) of 6.87°±0.2 °2θ and 21.11°±0.2 °2θ; and
wherein Form 4 is further characterized by an X-ray powder diffraction pattern comprising characteristic peaks at angles (°2θ) of 9.46°±0.2 °2θ and 22.63°±0.2°θ.

Figure 5:
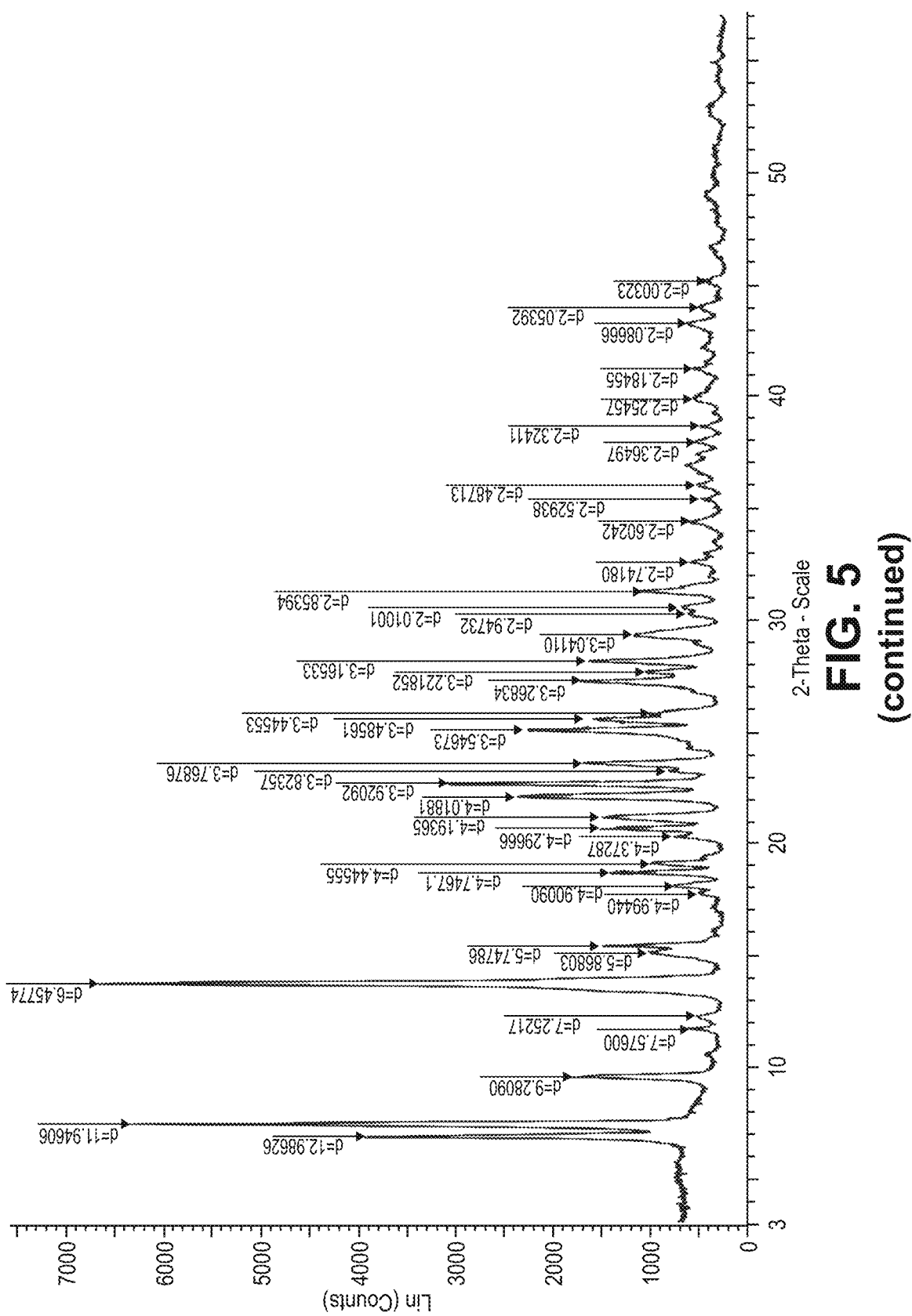
FIG. 5: An X-ray powder diffraction pattern of the crystal of a compound of Formula I wherein R=CH₂CH₃ (EL-001A2017120401)
Figure 6:
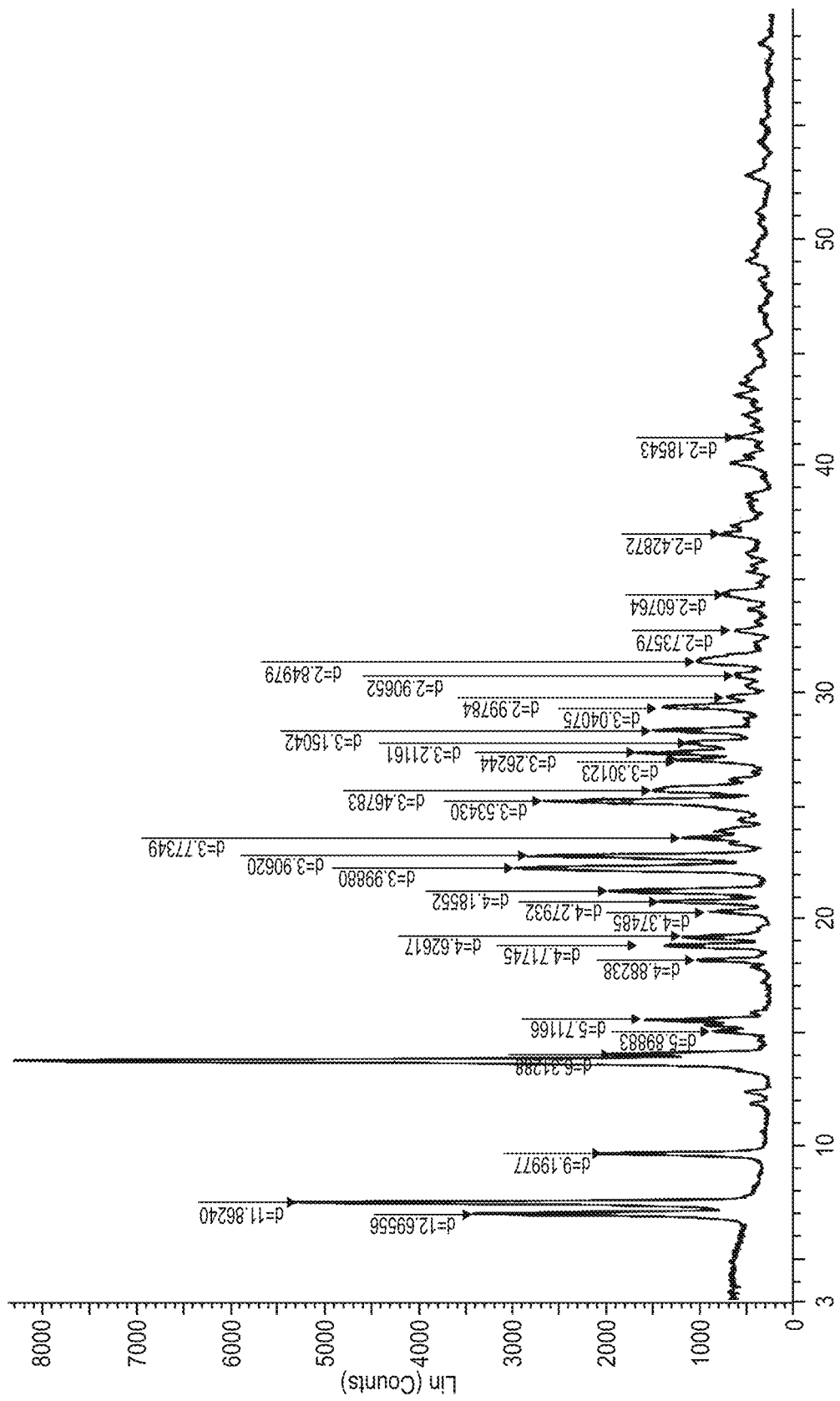
FIG. 6: An X-ray powder diffraction pattern of the crystal of a compound of Formula I wherein R=CH₂CH₃ (EL-001A2017120801)
Figure 7:
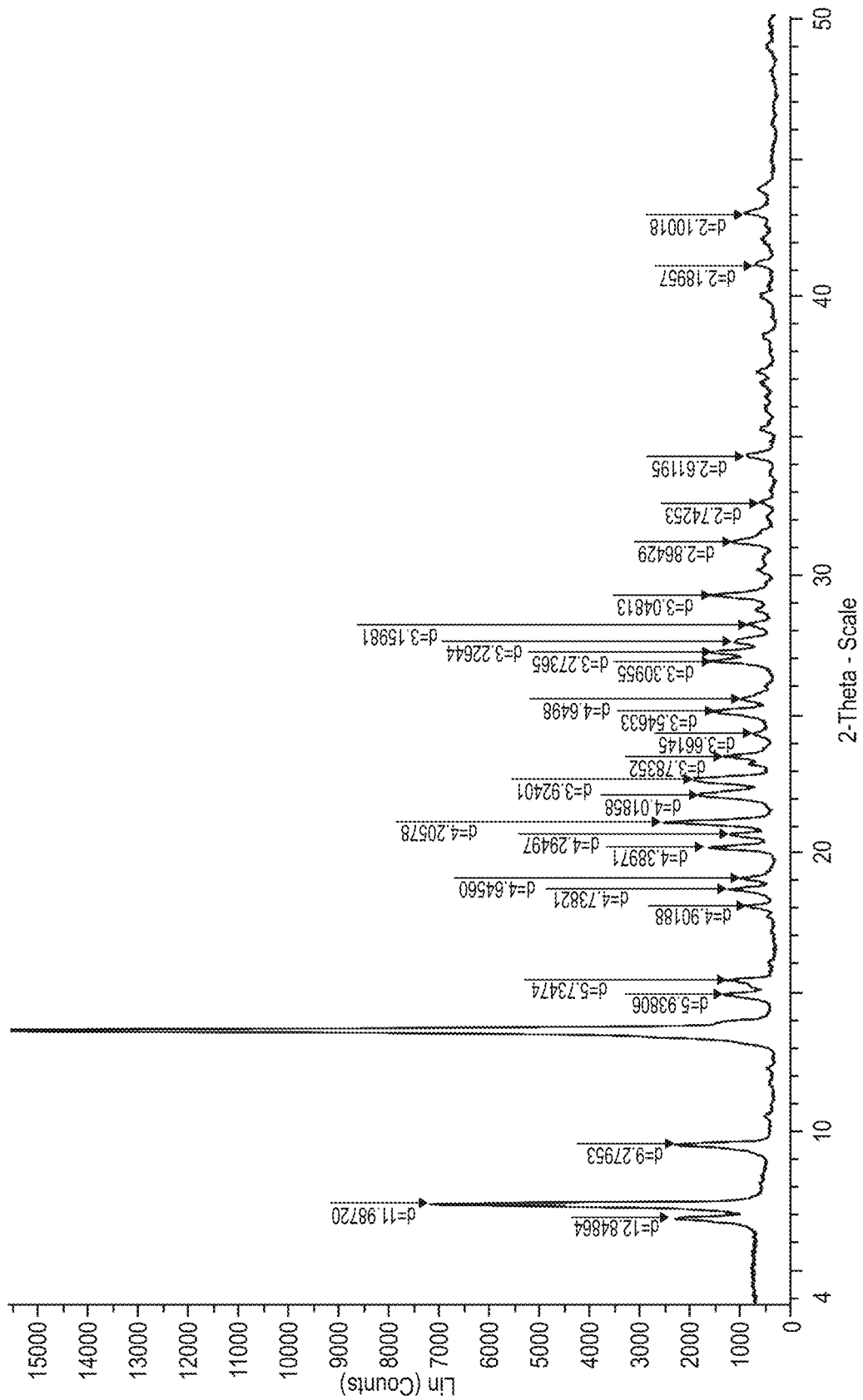
FIG. 7: An X-ray powder diffraction pattern of the crystal of a compound of Formula I wherein R=CH₂CH₃ (EL-001A20180105)

3. The crystal form according to claim 1, wherein the crystal form is Form 1, Form 2, Form 3, or Form 4;
wherein Form 1 is further characterized by an X-ray powder diffraction pattern as shown in FIG. 5;
wherein Form 2 is further characterized by an X-ray powder diffraction pattern as shown in FIG. 6;
wherein Form 3 is further characterized by an X-ray powder diffraction pattern as shown in FIG. 7; and
wherein Form 4 is further characterized by an X-ray powder diffraction pattern as shown in FIG. 8.

4. An intravenous anesthetic comprising the crystal form according to claim 1.

5. A pharmaceutical composition comprising a pharmaceutically acceptable excipient, carrier, and/or other auxiliary material and the crystal form according to claim 1.

6. A process for preparing the crystal form of ethyl (S)-3-(8-bromo-1-methyl-6-(pyridin-2-yl)-4H-benzo[f]imidazo[1,2-α][1,4]diazepin-4-yl)propanoate hydrochloride of Formula I according to claim 1:

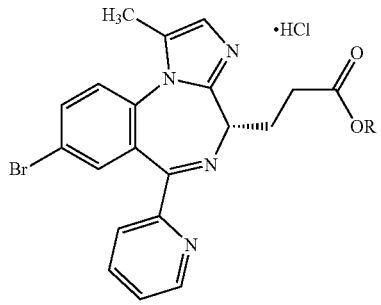

Formula I wherein R is CH$_2$CH$_3$;
wherein the crystal form is Form 1, Form 2, Form 3, or Form 4;
wherein Form 1 is characterized by an X-ray powder diffraction pattern comprising characteristic peaks at angles (°2θ) of 7.39°±0.2 °2θ and 13.70°±0.2 °2θ;
wherein Form 2 is characterized by an X-ray powder diffraction pattern comprising characteristic peaks at angles (°2θ) of 7.45°±0.2 °2θ and 13.71°±0.2 °2θ;
wherein Form 3 is characterized by an X-ray powder diffraction pattern comprising characteristic peaks at angles (°2θ) of 7.37°±0.2 °2θ and 13.63°±0.2 °2θ;
wherein Form 4 is characterized by an X-ray powder diffraction pattern comprising characteristic peaks at angles (°2θ) of 7.31°±0.2 °2θ and 13.56°±0.2 °2θ; and
wherein each X-ray powder diffraction pattern is measured on a diffractometer using CuKα radiation;
wherein the process comprises the following steps:
1) Dissolving ethyl (S)-3-(8-bromo-1-methyl-6-(pyridin-2-yl)-4H-benzo[f]imidazo[1,2-α][1,4]diazepin-4-yl)propanoate of Formula II-2:

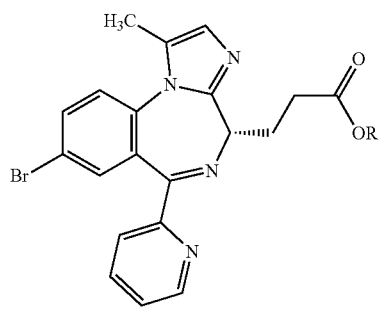

Formula II-2 wherein R is CH$_2$CH$_3$;
in an organic solvent 1 selected from the group consisting of methanol, ethanol, n-propanol, isopropanol, n-butanol, isobutanol, methyl acetate, ethyl acetate, propyl acetate, isopropyl acetate, butyl acetate, acetone, and butanone, or a mixture thereof, to form a solution;
2) At a temperature in the range of −20° C. to 60° C., adding an equimolar amount of a hydrochloric acid donor A selected from the group consisting of glycine hydrochloride, alanine hydrochloride, valine hydrochloride, a dry hydrochloric acid-methanol solution, a dry hydrochloric acid-ethanol solution, a dry hydrochloric acid-isopropanol solution, an acetyl chloride-methanol solution, an acetyl chloride-ethanol solution, an acetyl chloride-isopropanol solution, and a propionyl chloride-ethanol solution, to the solution of ethyl (S)-3-(8-bromo-1-methyl-6-(pyridin-2-yl)-4H-benzo[f]imidazo[1,2-α][1,4]diazepin-4-yl)propanoate of Formula II-2 formed in step 1) above, to form ethyl (S)-3-(8-bromo-1-methyl-6-(pyridin-2-yl)-4H-benzo[f]imidazo[1,2-a][1,4]diazepin-4-yl)propanoate hydrochloride of the following formula:

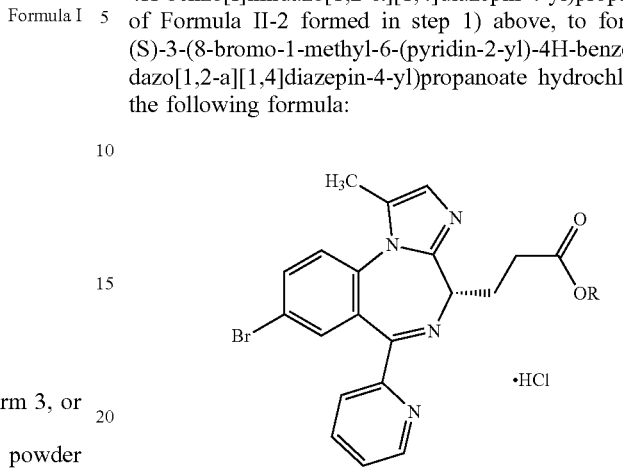

wherein R is CH$_2$CH$_3$;
3) Decolorizing the crude ethyl (S)-3-(8-bromo-1-methyl-6-(pyridin-2-yl)-4H-benzo[f]imidazo[1,2-α][1,4]diazepin-4-yl)propanoate hydrochloride formed in step 2) above; and
4) At a temperature in the range of −60° C. to 80° C., crystallizing the ethyl (S)-3-(8-bromo-1-methyl-6-(pyridin-2-yl)-4H-benzo[f]imidazo[1,2-α][1,4]diazepin-4-yl)propanoate hydrochloride formed in step 3) above in a crystallization solvent 1 selected from the group consisting of methanol, ethanol, n-propanol, isopropanol, n-butanol, isobutanol, ethyl ether, isopropyl ether, dioxane, methyl tert-butyl ether, methyl acetate, ethyl acetate, propyl acetate, isopropyl acetate, butyl acetate, acetone, butanone, n-pentane, hexane, heptane, petroleum ether, dichloromethane, chloroform, and 1,2-dichloroethane, or a mixture thereof, to obtain the crystal form of ethyl (S)-3-(8-bromo-1-methyl-6-(pyridin-2-yl)-4H-benzo[f]imidazo[1,2-α][1,4]diazepin-4-yl)propanoate hydrochloride of Formula I above:

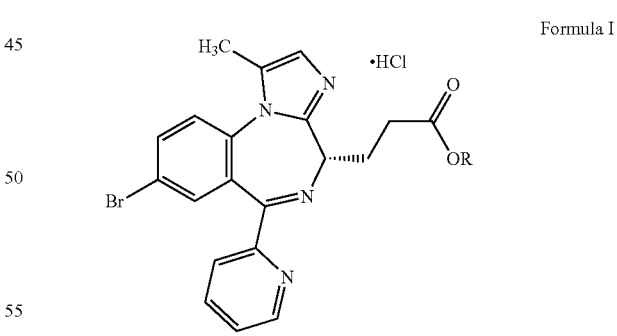

Formula I wherein R is CH$_2$CH$_3$.

7. The process according to claim 6, wherein the organic solvent 1 is selected from the group consisting of methanol, ethanol, n-propanol, isopropanol, n-butanol, isobutanol, methyl acetate, ethyl acetate, propyl acetate, isopropyl acetate, butyl acetate, acetone, and butanone, or a mixture thereof.

8. The process according to claim 6, wherein the hydrochloric acid donor A is selected from the group consisting of glycine hydrochloride, alanine hydrochloride, valine hydrochloride, a dry hydrochloric acid-methanol solution, a dry hydrochloric acid-ethanol solution, a dry hydrochloric acid-isopropanol solution, an acetyl chloride-methanol solution, an acetyl chloride-ethanol solution, an acetyl chloride-isopropanol solution, and a propionyl chloride-ethanol solution.

9. The process according to claim 8, wherein the hydrochloric acid donor A is selected from the group consisting of glycine hydrochloride, alanine hydrochloride, and valine hydrochloride.

10. The process according to claim 9, wherein the amount of glycine, alanine, or valine in the crystal form of ethyl (S)-3-(8-bromo-1-methyl-6-(pyridin-2-yl)-4H-benzo[f]imidazo[1,2-α][1,4]diazepin-4-yl)propanoate hydrochloride of Formula I is in the range of 0% (w/w) to 8% (w/w).

11. The process according to claim 8, wherein:
   (i) the hydrochloric acid donor A is a dry hydrochloric acid-methanol solution, a dry hydrochloric acid-ethanol solution, or a dry hydrochloric acid-isopropanol solution; or
   (ii) the hydrochloric acid donor A is an acetyl chloride-methanol solution, an acetyl chloride-ethanol solution, an acetyl chloride-isopropanol solution, or a propionyl chloride-ethanol solution.

12. The process according to claim 11, wherein:
   (i) the molar ratio of the dry hydrochloric acid-methanol solution, the dry hydrochloric acid-ethanol solution, or the dry hydrochloric acid-isopropanol solution to ethyl (S)-3-(8-bromo-1-methyl-6-(pyridin-2-yl)-4H-benzo[f]imidazo[1,2-α][1,4]diazepin-4-yl)propanoate hydrochloride of Formula I is in the range of 0.4:1 to 1:1; or
   (ii) the molar ratio of the acetyl chloride-methanol solution, the acetyl chloride-ethanol solution, the acetyl chloride-isopropanol solution, or the propionyl chloride-ethanol solution to ethyl (S)-3-(8-bromo methyl-6-(pyridin-2-yl)-4H-benzo imidazo[1,2-α][1,4]diazepin-4-yl)propanoate hydrochloride of Formula I is in the range of 0.4:1 to 1:1; or
   (iii) the molar ratio of the glycine hydrochloride, alanine hydrochloride, or valine hydrochloride to the crystal form of ethyl (S)-3-(8-bromo-1-methyl-6-(pyridin-2-yl)-4H-benzo[f]imidazo[1,2-α][1,4]diazepin-4-yl)propanoate hydrochloride of Formula I is in the range of 1:1 to 10:1.

13. The process according to claim 6, wherein the crystallization solvent 1 is selected from the group consisting of methanol, ethanol, n-propanol, isopropanol, n-butanol, isobutanol, ethyl ether, isopropyl ether, dioxane, methyl tert-butyl ether, methyl acetate, ethyl acetate, propyl acetate, isopropyl acetate, butyl acetate, acetone, butanone, n-pentane, hexane, heptane, petroleum ether, dichloromethane, chloroform, and 1,2-dichloroethane, or a mixture thereof.

14. The process according to claim 6, wherein:
   (i) step 2) is performed at a temperature in the range of −10° C. to 30° C.; and
   (ii) step 4) is performed at a temperature in the range of −20° C. to 60° C.

15. A crystal form of ethyl (S)-3-(8-bromo-1-methyl-6-(pyridin-2-yl)-4H-benzo[f]imidazo[1,2-α][1,4]diazepin-4-yl)propanoate hydrochloride of Formula I:

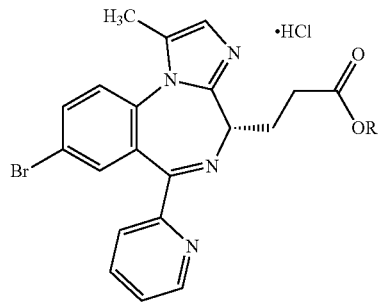

Formula I wherein R is $CH_2CH_3$;
wherein the crystal form is Form 5;
wherein Form 5 is characterized by an X-ray powder diffraction pattern comprising characteristic peaks at angles (° 2θ) of 7.41°±0.2 °2θ, 9.24°±0.2 °2θ, 12.71°±0.2 °2θ, 13.64°±0.2 °2θ, 15.06°±0.2 °2θ, 18.30°±0.2 °2θ, 18.72°±0.2 °2θ, 21.59°±0.2 °2θ, 22.18°±0.2 °2θ, and 25.74°±0.2 °2θ; and
wherein the X-ray powder diffraction pattern is measured on a diffractometer using CuKα radiation.

16. The crystal form according to claim 15, wherein the crystal form is further characterized by an X-ray powder diffraction pattern comprising characteristic peaks at angles (°2θ) of 9.52°±0.2 °2θ, 11.69°±0.2 °2θ, 20.90°±0.2 °2θ, 22.60°±0.2 °2θ, 23.65°±0.2 °2θ, 24.26°±0.2 °2θ, 26.40°±0.2 °2θ, 28.43°±0.2 °2θ, and 29.35°±0.2 °2θ.

17. The crystal form according to claim 15, wherein the crystal form is further characterized by an X-ray powder diffraction pattern as shown in FIG. 9.

18. An intravenous anesthetic comprising the crystal form according to claim 15.

19. A crystal form of ethyl (S)-3-(8-bromo-1-methyl-6-(pyridin-2-yl)-4H-benzo[f]imidazo[1,2-α][1,4]diazepin-4-yl)propanoate hydrochloride of Formula I:

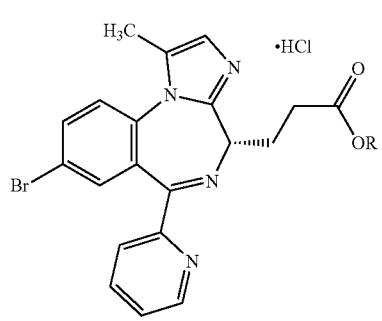

Formula I wherein R is $CH_2CH_3$;
wherein the crystal form is Form 6, Form 7, Form 8, or Form 9;
wherein Form 6 is characterized by an X-ray powder diffraction pattern comprising characteristic peaks at angles (°2θ) of 7.45°±0.2 °2θ and 13.73°±0.2 °2θ;
wherein Form 7 is characterized by an X-ray powder diffraction pattern comprising characteristic peaks at angles (°2θ) of 13.36°±0.2 °2θ and 13.66°±0.2 °2θ;
wherein Form 8 is characterized by an X-ray powder diffraction pattern comprising characteristic peaks at angles (°2θ) of 7.34°±0.2 °2θ and 13.62°±0.2 °2θ;

wherein Form 9 is characterized by an X-ray powder diffraction pattern comprising characteristic peaks at angles (°2θ) of 7.31°±0.2 °2θ and 13.64°±0.2 °2θ; and
wherein each X-ray powder diffraction pattern is measured on a diffractometer using CuKα radiation.

20. The crystal form according to claim 19, wherein the crystal form is Form 6, Form 7, Form 8, or Form 9;
wherein Form 6 is further characterized by an X-ray powder diffraction pattern comprising characteristic peaks at angles (°2θ) of 9.64°±0.2 °2θ and 22.22°±0.2 °2θ;
wherein Form 7 is further characterized by an X-ray powder diffraction pattern comprising characteristic peaks at angles (°2θ) of 7.38°±0.2 °2θ and 22.17°±0.2 °2θ;
wherein Form 8 is further characterized by an X-ray powder diffraction pattern comprising characteristic peaks at angles (°2θ) of 6.84°±0.2 °2θ and 22.61°±0.2 °2θ; and
wherein Form 9 is further characterized by an X-ray powder diffraction pattern comprising characteristic peaks at angles (°2θ) of 6.66°±0.2 °2θ and 22.47°±0.2 °2θ.

Figure 10:
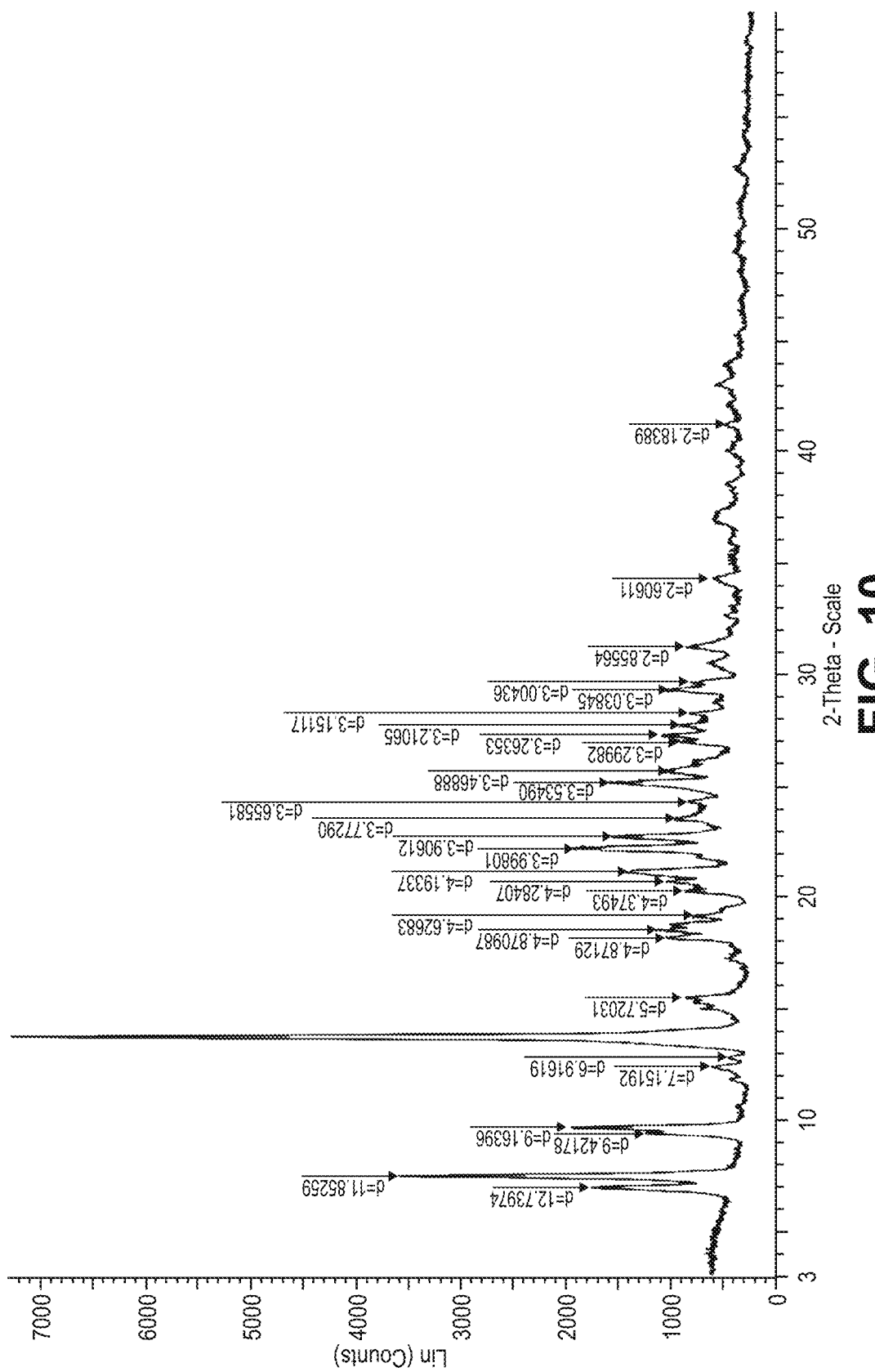
FIG. 10: An X-ray powder diffraction pattern of the crystal of a compound of Formula I wherein R=CH₂CH₃ (EL-001AG2017121801)
Figure 12:
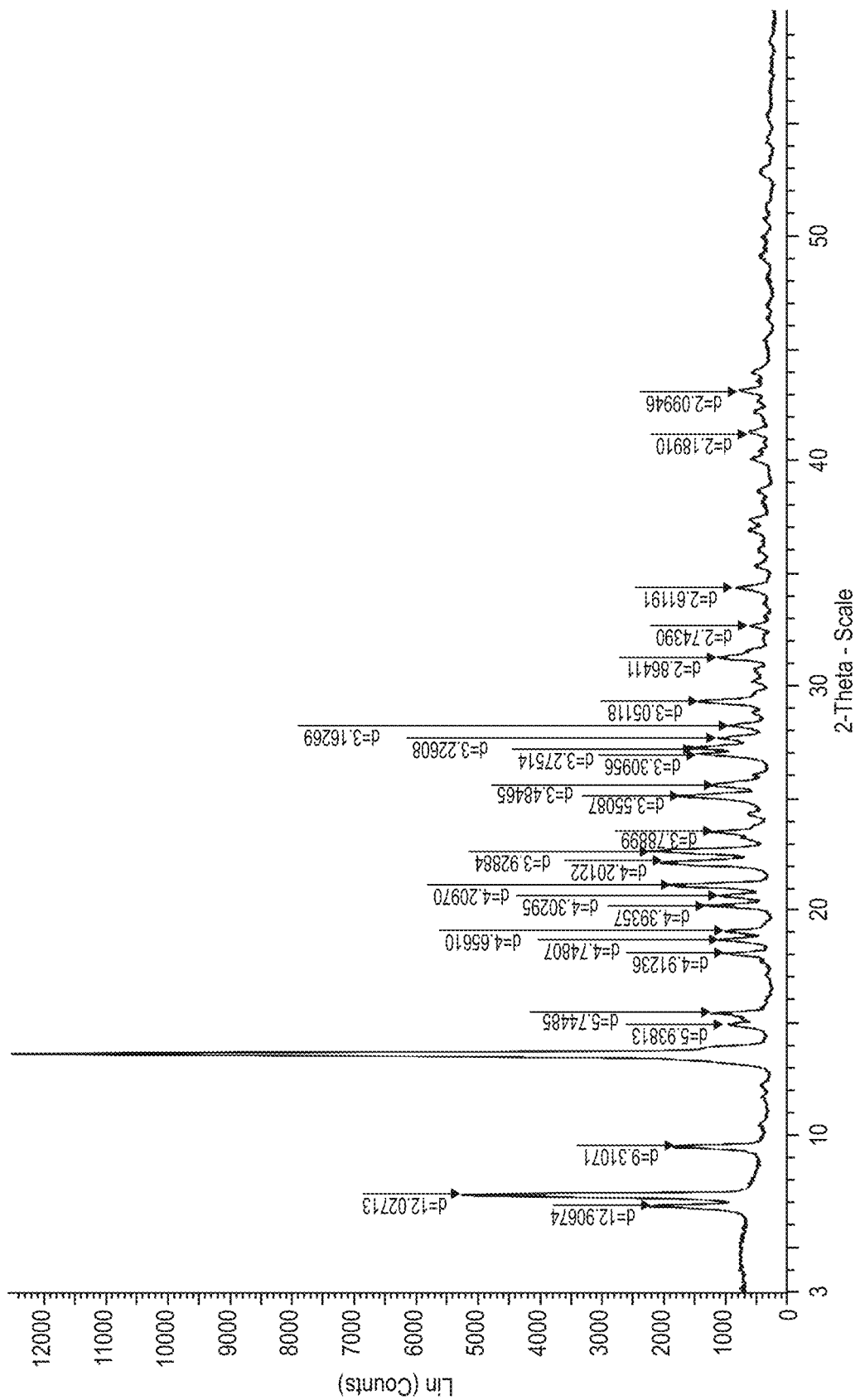
FIG. 12: An X-ray powder diffraction pattern of the crystal of a compound of Formula I wherein R=CH₂CH₃ (EL-001AG2017122702LJ)

21. The crystal form according to claim 19, wherein the crystal form is Form 6, Form 7, Form 8, or Form 9;
wherein Form 6 is further characterized by an X-ray powder diffraction pattern as shown in FIG. 10;
wherein Form 7 is further characterized by an X-ray powder diffraction pattern as shown in FIG. 11;
wherein Form 8 is further characterized by an X-ray powder diffraction pattern as shown in FIG. 12; and
wherein Form 9 is further characterized by an X-ray powder diffraction pattern as shown in FIG. 13.

22. An intravenous anesthetic comprising the crystal form according to claim 19.

* * * * *